(12) United States Patent
Boehlow et al.

(10) Patent No.: US 12,215,070 B2
(45) Date of Patent: Feb. 4, 2025

(54) CYANOCARBON COMPOSITIONS

(71) Applicant: Ascend Performance Materials Operations LLC, Houston, TX (US)

(72) Inventors: Todd R. Boehlow, Houston, TX (US); Benjamin Haseltine, Houston, TX (US); Jefferson Thomas Ebert, Houston, TX (US); Sanjay Dube, Houston, TX (US); Darrick Elmore, Houston, TX (US)

(73) Assignee: Ascend Performance Materials Operations LLC, Houston, TX (US)

( * ) Notice: Subject to any disclaimer, the term of this patent is extended or adjusted under 35 U.S.C. 154(b) by 707 days.

(21) Appl. No.: 16/953,521

(22) Filed: Nov. 20, 2020

(65) Prior Publication Data

US 2021/0155579 A1 May 27, 2021

Related U.S. Application Data

(60) Provisional application No. 62/939,255, filed on Nov. 22, 2019.

(51) Int. Cl.
   *C07C 255/05* (2006.01)
(52) U.S. Cl.
   CPC .................. *C07C 255/05* (2013.01)
(58) Field of Classification Search
   None
   See application file for complete search history.

(56) References Cited

U.S. PATENT DOCUMENTS

2013/0157119 A1   6/2013   Shimura et al.
2020/0369602 A1   11/2020  Dube et al.

FOREIGN PATENT DOCUMENTS

| EP | 1460054 A1 | 9/2004 |
| JP | S62270550 A | 11/1987 |
| JP | 2003183239 A | 7/2003 |
| JP | 2003192631 A | 7/2003 |
| JP | 2005072182 A | 3/2005 |
| WO | 2020242931 A1 | 12/2020 |

OTHER PUBLICATIONS

Baizer et al. (J. Org. Chem., 1965, 30(5), 1357) (Year: 1965).*
Bishop (Atoms First Version of An Introduction to Chemistry, Chapter 1.5, 2019, Chiral Publishing Company, https://preparatorychemistry.com/Bishop_Atoms_First.htm) (Year: 2019).*

* cited by examiner

*Primary Examiner* — Sudhakar Katakam
*Assistant Examiner* — Jennifer C Sawyer
(74) *Attorney, Agent, or Firm* — COZEN O'CONNOR

(57) ABSTRACT

The disclosure relates to the cyanocarbon compositions and processes for producing the same. The cyanocarbon compositions comprise tricyanohexane and one or more coproducts of the tricyanohexane production reaction. Exemplary coproducts include tetracyano compounds, cyanoalkenes, cyanooximes, cyanoamides, and combinations thereof.

15 Claims, 5 Drawing Sheets

CYANOCARBON COMPOSITIONS

REFERENCE TO RELATED APPLICATION

This application claims priority to U.S. Provisional Application No. 62/939,255, filed on Nov. 22, 2019, which is incorporated herein by reference.

FIELD

The present disclosure relates generally to cyanocarbon compositions. In particular, the present disclosure relates to cyanocarbon compositions comprising tricyanohexane (TCH) and specific coproducts.

BACKGROUND

Cyanocarbons, e.g., organic compounds having cyano or nitrile functional groups, are known and widely used in various application. For example, many cyanocarbons are used as monomers to prepare various polymers, such as nylon, polyacrylonitrile, acrylonitrile butadiene rubber, or acrylonitrile butadiene styrene. Some cyanocarbons are also used as electrolyte solution additives, e.g., in secondary cells, e.g., rechargeable batteries or storage batteries. In particular, cyanocarbons, such as TCH, have been found to stabilize conventional electrolyte solutions against oxidation at high voltages. As a result, cyanocarbon additives have played a crucial role in the development of novel secondary cells, such as lithium ion batteries.

However, the performance of many typical cyanocarbon compositions, while suitable for conventional applications, may be insufficient in more advanced applications, e.g., in more advanced lithium ion battery configurations. For example, conventional cyanocarbon compositions may suffer from the presence and/or propensity to form of water. Water has been found to detrimentally impact the functioning of cyanocarbon composition, e.g., damaging to electrolyte solutions in lithium ion batteries where it may promote the formation of corrosive compounds such as hydrogen fluoride. Conventional cyanocarbon composition may also suffer from the presence and/or propensity to form gaseous components, e.g., hydrogen gas, which contribute to the instability and/or dangerousness of the compositions. Further, conventional cyanocarbon compositions suffer from the problems of insufficient chemical identifiers, which may prohibit identification of the compositions in processes/applications in which the cyanocarbon compositions are subsequently employed.

Thus, the need exists for cyanocarbon compositions which prevent the formation or buildup of water, which prevent the formation or buildup of gaseous components, and which are readily identifiable.

SUMMARY

The present disclosure relates to cyanocarbon compositions comprising (at least 92 wt. %) tricyanohexane (TCH) and (from 1 wppm to 10 wt. % of) specific tricyanohexane coproducts, e.g., an isomer of tricyanohexane, a tetracyano compound, a tricyanoalkene, a (cyanoethyl)amine (tri-(cyanoethyl)amine), or adipinitrile, or combinations thereof. In some aspects, the disclosure describes a cyanocarbon composition comprising: tricyanohexane; and an isomer of tricyanohexane, In some cases, the weight ratio of tricyanohexane to the isomer is optionally at least 5:1. In some aspects, the coproduct comprises a tetracyano compound having the chemical formula $C_xH_{2x-2}(CN)_4$; wherein x is from 5 to 10. In some aspects, the coproduct comprises a cyanooxime having the chemical structure:

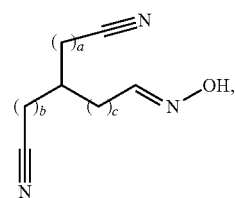

wherein a is 0 to 3, b is 1 to 3, and c is 1 to 4. In some aspects, the coproduct comprises a cyano-compound having the chemical structure

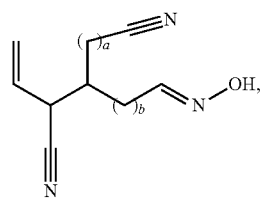

wherein a is from 1 to 3, and b is from 1 to 4. In some aspects, the disclosure describes a cyanocarbon composition comprising: at least 85 wt. % tricyanohexane; a first cyano-compound having the chemical formula $C_xH_{2x-2}(CN)_4$; a second cyano-compound having the chemical formula $C_6H_{11}(CN)_2(CNOH)$; and a third cyano-compound having the chemical formula $C_xH_{2x-3}(CN)_2(CNOH)$ wherein x is independently from 5 to 10; wherein the weight ratio of the first cyano-compound to the second cyano-compound is less than 1; wherein the weight ratio of the second cyano-compound to the second cyano-compound is greater than 1. In some aspects, the disclosure describes a cyanocarbon composition, comprising: tricyanohexane a tricyanohexane coproduct having a molecular weight ranging from 105 amu to 215 amu, e.g., from 145 to 180 amu. In some aspects, the disclosure describes a cyanocarbon composition, comprising: tricyanohexane; and an in situ-formed coproduct comprising an isomer of tricyanohexane, a cyanoethylamine, an oxime of tricyanohexane, an amide of tricyanohexane, or a tetracyanoalkane, or combinations thereof. In some cases, the cyanocarbon composition comprises at least 92 wt. % tricyanohexane, from 0.1 wt % to 10 wt % of an isomer of tricyanohexane, wherein the weight ratio of tricyanohexane to the isomer is at least 5:1, and from 500 ppm to 1 wt % adiponitrile. In some cases, the cyanocarbon composition comprises at least 92 wt. % tricyanohexane, from 0.5 wt % to 7 wt % of an isomer of tricyanohexane, and from 0.05 ppm to 2 wt. % of a tetracyano compound. In some aspects, the cyanocarbon composition comprises at least 92 wt. % tricyanohexane, preferably at least 95 wt % tricyanohexane. In some aspects, the isomer of tricyanohexane comprises 1,2,3-tricyanohexane, 1,2,6-tricyanohexane, 1,3,4-tricyanohexane, 1,3,5-tricyanohexane, 1,3,6-tricyanohexane, 1,4,5-tricyanohexane, or 2,3,5-tricyanohexane, or combinations thereof. In some aspects, the cyanoethylamine comprises tri-(cyanoethyl)amine. In some aspects, the cyanocarbon composition comprises less than 0.1 wt. % isomer of tricyanohexane. In some aspects, the cyanocarbon composition comprises less than 0.1 wt. % tetracyanoalkane. In some aspects, the cyanocarbon composition comprises less than 0.1 wt. % tricyanoalkene. In some aspects, the cyanocarbon composition comprises less than 0.1 wt. % tri-(cyanoethyl) amine. In some aspects, the cyanocarbon composition comprises less than 0.1 wt. % cyanooxime. In some aspects, the cyanocarbon composition comprises less than 0.1 wt. % tricyanohexane coproduct having a molecular weight ranging from 145 to 180 amu. In some aspects, the cyanocarbon composition comprises less than 0.1 wt. % in-situ formed coproduct. In some embodiments, the composition comprises less than 0.1 wt. % tricyanohexane coproduct having a molecular weight ranging from 105 amu to 215 amu. In some embodiments, the composition comprises at least 92 wt. % tricyanohexane, from 0.5 wt % to 7 wt % of an isomer of tricyanohexane, and from 0.05 ppm to 2 wt. % of a tetracyano compound, and wherein the isomer of tricyanohexane and the tetracyano compound are in situ-formed.

BRIEF DESCRIPTION OF THE DRAWINGS

The disclosure is described in detail below with reference to the appended drawings, wherein like numerals designate similar parts.

DETAILED DESCRIPTION

Introduction

Figure 1:
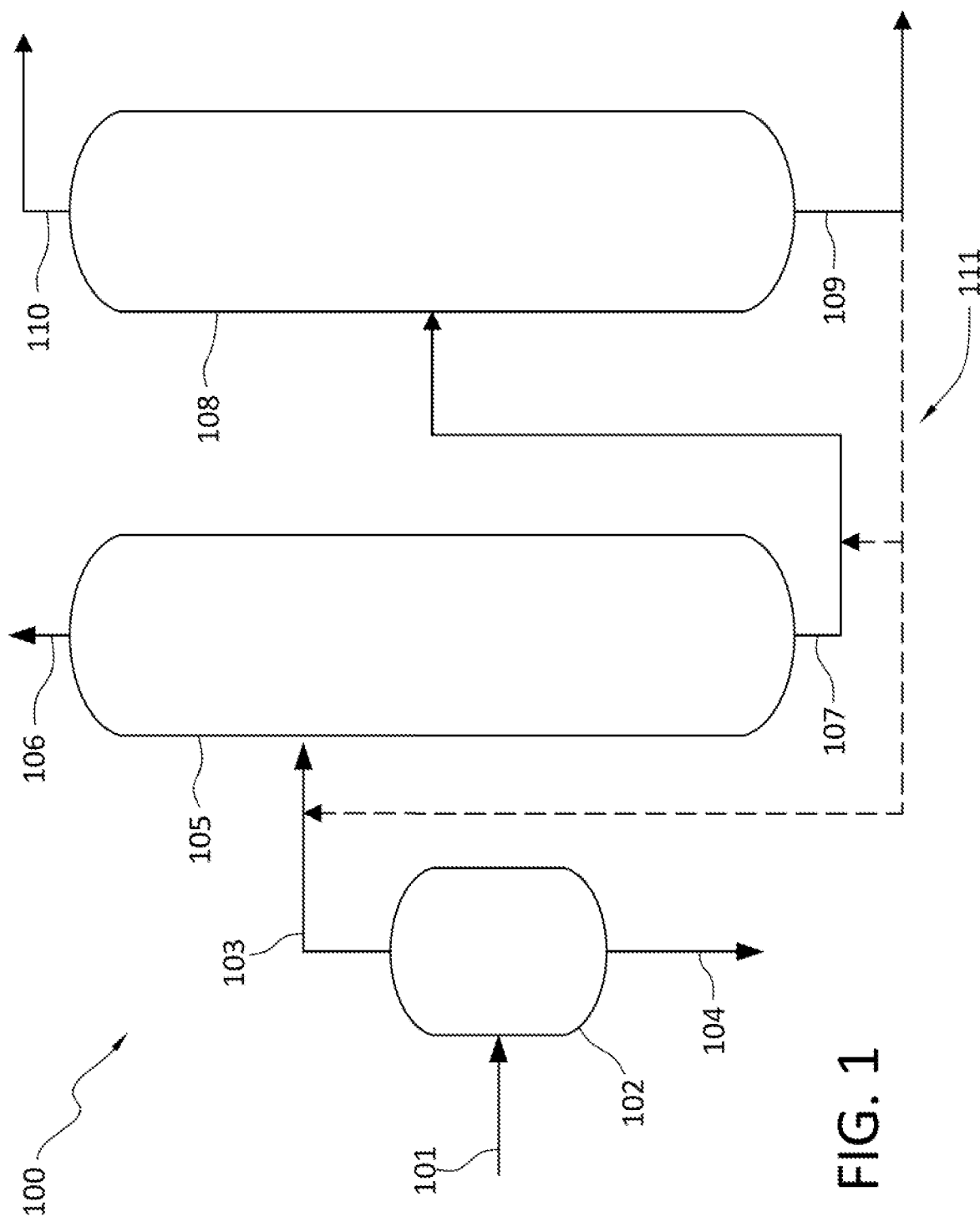
FIG. 1 depicts a schematic overview of an embodiment of the process of purifying TCH.

Conventional cyanocarbon compositions are known as additives in electrolyte solutions. As noted above, however, the performance of many cyanocarbon compositions may be insufficient in more advanced applications, e.g., in more advanced lithium ion batteries.

The inventors have now found that some cyanocarbon compositions, e.g., those containing tricyanohexane (TCH), e.g., 1,3,6-tricyanohexane, and specific combinations of coproducts, demonstrate improved and synergistic performance over the conventional compositions that do not contain the particular coproducts. For example, the disclosed cyanocarbon compositions have been found to show significant improvements in preventing the formation and/or buildup of water and various gaseous components, which provides for better stability and safety in lithium battery applications.

Without being bound by theory, it is believed that some combinations of the disclosed coproducts, along with the TCH, (and optionally in specific component amounts) provide for unexpected amounts of additional nitrile functionality, which, in turn, allows unexpected performance improvements, e.g., stabilization. It is believed that the nitrile moieties of TCH and the various coproducts described herein improve the functioning of the cyanocarbon composition to scavenge various impurities. For example, it is believed that the (higher numbers of) cyano functional groups, e.g., nitrile moieties, (in some cases as provided by the coproducts) exhibit improved hygroscopic activity. TCH (in combination with the disclosed coproducts) for example, has been found to be especially hygroscopic and particularly efficient in scavenging water present in the electrolyte solutions that comprise the cyanocarbon composition. This hygroscopic activity helps to prevent the formation and/or buildup of water. The cyano functional group or groups of the coproducts may synergistically work in conjunction with TCH to achieve unexpected performance improvements. For example, in some battery-related applications where electrodes (cathodes and/or anodes) are involved, the combination of the coproducts and the TCH has been found to interact during the formation step to create a robust cathode electrolyte interface layer. Such a layer may advantageously reduce degradation of electrode (cathode) and or of chemicals that make up an electrolyte. Stated another way, the combinations of coproducts disclosed herein has been found to beneficially provide for superior cathode electrode electrolyte performance, as opposed to other, conventional compounds, which would have a detrimental effects on the electrodes, e.g., breakdowns during cycling, which would create gases and adverse molecules like HF, which then turn attack the cathode. Also, the combination has unexpectedly been found to provide the ability to scavenge water, which is valuable in many applications, including battery-related applications. Traditional cyanocarbon compositions do not comprise the disclosed coproducts, and as such do not comprise (as many of) the aforementioned cyano functional groups. Thus, these cyanocarbon compositions fail to provide for the aforementioned performance improvements.

In addition, the inventors have also found that the aforementioned coproducts in the cyanocarbon composition advantageously function as a compositional indicator of the process by which the cyanocarbon composition was made, thus providing for a chemical fingerprint that can be used as an analytical tool in compositions and processes/applications in which the cyanocarbon compositions are subsequently employed. For example, the presence of the disclosed coproducts in the cyanocarbon compositions may indicate a commercial grade or specific commercial product, which may allow a producer to better analyze its resultant products, e.g., its particular electrolyte solutions.

The present disclosure relates to cyanocarbon compositions, in particular, to cyanocarbon compositions comprising TCH and one or more coproducts from a specific TCH reaction and purification scheme designed accordingly. One example is the reaction and purification scheme disclosed in U.S. patent application Ser. No. 16/880,717, entitled Tricyanohexane Purification Methods, which is hereby incorporated by reference. These processes contribute to the unique, synergistic combinations of coproducts (in the disclosed amounts) discussed herein. Conventional processes do not employ the same steps and/or process conditions, and, as such, do not and cannot yield the aforementioned synergistic cyanocarbon compositions. The TCH coproducts of the cyanocarbon compositions may comprise isomers of tricyanohexane; compounds having similar molecular weight to tricyanohexane; tetracyanocompounds; cyanoalkenes; cyanoamines; and/or cyanoamides; or combinations thereof.

In some embodiments, the present disclosure further relates to the processes for producing (via reaction) and/or purifying the cyanocarbon compositions described herein. The production and purification processes described herein have been found to produce a high concentration of TCH as well as of the specific combinations of coproducts (optionally in the disclosed amounts).

Cyanocarbon Compositions

The cyanocarbon compositions may comprise TCH and various coproducts. The cyanocarbon compositions may generally comprise TCH in high amounts, e.g., the compositions will be high purity TCH compositions. TCH, in some cases, is a chemical compound having the chemical formula $C_6H_{11}(CN)_3$. In some embodiments, the majority component TCH is 1,3,6-tricyanohexane.

As noted above, TCH may be the primary component of the cyanocarbon composition. Said another way, TCH is the majority component in the cyanocarbon composition.

In one embodiment, the cyanocarbon composition comprises at least 85 wt. % TCH, e.g., at least 88 wt. %, at least 90 wt. %, at least 92 wt. %, or at least 95 wt. %. In terms of upper limits, the cyanocarbon composition may comprise less than 100 wt. % TCH, e.g., less than 99.9 wt. %, less than 99 wt. %, or less than 98.5 wt. %. In terms of ranges, the cyanocarbon composition may comprise from 85 wt. % to 100 wt. % TCH, from 85 wt. % to 99.9 wt. %, from 85 wt. % to 99 wt. %, from 85 wt. % to 98.5 wt. %, from 88 wt. % to 100 wt. %, from 88 wt. % to 99.9 wt. %, from 88 wt. % to 99 wt. %, from 88 wt. % to 98.5 wt. %, from 90 wt. % to 99.9 wt. %, from 90 wt. % to 99 wt. %, from 90 wt. % to 98.5 wt. %, from 92 wt. % to 100 wt. %, from 92 wt. % to 99.9 wt. %, from 92 wt. % to 99 wt. %, from 92 wt. % to 98.5 wt. %, from 95 wt. % to 100 wt. %, from 95 wt. % to 99.9 wt. %, from 95 wt. % to 99 wt. %, or from 95 wt. % to 98.5 wt. %.

The content of the tricyanohexane coproduct present in the cyanocarbon composition is not particularly limited and may vary widely. In one embodiment, the cyanocarbon composition comprises from 1 wppb to 10 wt. % tricyanohexane coproduct, e.g., from 1 wppb to 5 wt. %, from 1 wppb to 3 wt. %, from 1 wppb to 1 wt. %, from 1 wppb to 0.5 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, 100 ppm to 0.5 wt %, 200 ppm to 0.5 wt %, 200 ppm to 0.3 wt %, from 500 ppm to 2 wt %, from 500 ppm to 1 wt %, from 0.1 wt % to 1 wt %, from 1 wppb to 10 wt. %, 1 wppm to 7 wt. %, 10 wppm to 5 wt. %, 1 wppb to 1 wt. %, from 0.15 wt % to 0.9 wt %, from 0.1 wt % to 0.7 wt %, from 0.1 wt % to 0.5 wt %, from 0.25 wt % to 1 wt %, from 0.25 wt % to 75 wt %, from 50 ppm to 0.5 wt. %, from 0.05 wt % to 1 wt %, from 0.05 wt % to 0.8 wt %, from 0.1 wt. % to 1 wt %, from 0.2 wt. % to 0.9 wt. %, from 0.05 wt % to 0.6 wt %, from 0.1 wt. % to 0.3 wt %, from 0.01 wt. % to 0.5 wt. %, from 0.1 wt. % to 0.8 wt %, from 0.05 wt. % to 0.1 wt. %, from 0.05 wt. % to 1 wt. %, from 0.2 wt. % to 0.6 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb tricyanohexane coproduct, e.g., greater than 10 wppb, greater than 100 wppb, greater than 500 wppb, greater than 1 ppm, greater than 10 ppm, greater than 50 ppm, greater than 100 wppm, or greater than 200 wppm, greater than 0.1 wt. %, greater than 0.2 wt. %, greater than 1 wt. %, greater than 0.05 wt %, greater than 0.1 wt %, or greater than 0.25 wt %. In terms of upper limits, the cyanocarbon composition may comprise less than 1 wt. % tricyanohexane coproduct, e.g., less than 0.5 wt. %, less than 1 wt. %, less than 0.8 wt. %, less than 0.9 wt. %, less than 0.6 wt. %, less than 0.3 wt. %, less than 0.1 wt. %, less than 0.05 wt. %, or less than 0.01 wt. %. These ranges and limits are applicable to the individual coproducts described herein as well as combinations of these coproducts.

Molecular Weight

In some embodiments, the cyanocarbon composition comprises a tricyanohexane coproduct having a similar molecular weight to tricyanohexane. For example, the tricyanohexane coproduct may result from a particular TCH production and/or purification scheme. The inventors have found that the presence of these tricyanohexane coproduct(s) may advantageously provide for increased stabilization effect, e.g., increased or improved hygroscopic activity and/or the aforementioned cathode electrolyte layer benefits, by the cyanocarbon composition.

In one embodiment, the tricyanohexane coproduct has a molecular weight from 100 amu to 220 amu, e.g., from 105 amu to 215 amu, from 145 amu to 180 amu, from 145 amu to 178 amu, from 145 amu to 175 amu, from 145 amu to 172 amu, from 145 amu to 170 amu, from 148 amu to 180 amu, from 148 amu to 178 amu, from 148 amu to 175 amu, from 148 amu to 172 amu, from 148 amu to 170 amu, from 150 amu to 180 amu, from 150 amu to 178 amu, from 150 amu to 175 amu, from 150 amu to 172 amu, from 150 amu to 170 amu, from 152 amu to 180 amu, from 152 amu to 178 amu, from 152 amu to 175 amu, from 152 amu to 172 amu, from 152 amu to 170 amu, from 155 amu to 180 amu, from 155 amu to 178 amu, from 155 amu to 175 amu, from 155 amu to 172 amu, or from 155 amu to 170 amu. In terms of lower limits, the tricyanohexane coproduct may have a molecular weight greater than 100 amu, e.g., greater than 105 amu, greater than 145 amu, greater than 148 amu, greater than 150 amu, greater than 152 amu, or greater than 155 amu. In terms of upper limits, the tricyanohexane coproduct may have a molecular weight less than 220 amu, e.g., less than 215a mu, less than 180 amu, e.g., less than 178 amu, less than 175 amu, less than 172 amu, or less than 170 amu.

In one embodiment, the tricyanohexane coproduct has a molecular weight that is from 85% to 115% the molecular weight of tricyanohexane, e.g., from 85% to 112%, from 85% to 110%, from 85% to 108%, from 85% to 105%, from 88% to 115%, from 88% to 112%, from 88% to 110%, from 88% to 108%, from 88% to 105%, from 90% to 115%, from 90% to 112%, from 90% to 110%, from 90% to 108%, from 90% to 105%, from 92% to 115%, from 92% to 112%, from 92% to 110%, from 92% to 108%, from 92% to 105%, from 95% to 115%, from 95% to 112%, from 95% to 110%, from 95% to 108%, or from 95% to 105%. The tricyanohexane coproduct may have a molecular weight that is less than 115% the molecular weight of tricyanohexane, e.g., less than 112%, less than 110%, less than 108%, or less than 105%. The tricyanohexane coproduct may have a molecular weight that is greater than 85% the molecular weight of tricyanohexane, e.g., greater than 88%, greater than 90%, greater than 92%, or greater than 95%

Isomers of Tricyanohexane

In some embodiments, the cyanocarbon composition comprises an isomer of tricyanohexane, e.g., not 1,3,6-tricyanohexane. The particular isomer of tricyanohexane may have the chemical formula $C_9H_{11}N_3$, and may have another arrangement, e.g., structural isomer, of the three cyano, or nitrile, groups on a chain of six carbon atoms. For example, the cyanocarbon composition may comprise 1,3, 6-tricyanohexane (as the majority component TCH) and 1,3,5-tricyanohexane as the isomer.

The inventors have found that the presence of tricyanohexane isomer or isomers advantageously provides for further stabilization conventional electrolyte solutions against oxidation at high voltages. Without being bound by theory, it is believed that the arrangement of three nitrile groups on the tricyanohexane isomer may synergistically improve the stabilization effects of the majority component TCH. For example, the three nitrile groups may contribute to increased or improved hygroscopic activity and/or the aforementioned cathode electrolyte layer benefits.

In some embodiments, the tricyanohexane isomer comprises 1,2,3-tricyanohexane, 1,2,6-tricyanohexane, 1,3,4-tricyanohexane, 1,3,5-tricyanohexane, 1,3,6-tricyanohexane, 1,4,5-tricyanohexane, or 2,3,5-tricyanohexane, or combinations thereof. In some embodiments, the tricyanohexane comprises 1,3,5-tricyanohexane.

In some embodiments, the isomer may comprise a constitutional isomer of tricyanohexane. For example, the isomer may comprise an amino-compound with cyano functional groups.

In some embodiments, the isomer may comprise a stereoisomer of tricyanohexane. In some embodiments, for example, the tricyanohexane of the cyanocarbon composition may include one or more chiral centers, and the isomer of tricyanohexane may be an enantiomer. For example, 1,3,6-tricyanohexane comprise one chiral center, and 1,3,6-tricyanohexane therefore defines two enantiomers. Thus, in some embodiments of the cyanocarbon composition, the tricyanohexane is 1,3,6-tricyanohexane, and the isomer of tricyanohexane is an enantiomer thereof. In some embodiments, the tricyanohexane may include multiple chiral centers, and the isomer of tricyanohexane may be one or more stereoisomers, e.g., enantiomers and/or diastereomers.

The content of the isomer of tricyanohexane present in the cyanocarbon composition is not particularly limited and may vary widely. The content of the isomer may be described by the weight ratio of tricyanohexane to the isomer. In one embodiment, for example, the cyanocarbon composition comprises tricyanohexane and an isomer thereof, and the weight ratio of tricyanohexane to the isomer is at least 5:1, e.g., at least 8:1, at least 10:1, at least 15:1, at least 20:1, or at least 25:1. In terms of upper limits, the weight ratio of tricyanohexane to the isomer may be less than 100:1, e.g., less than 95:1, less than 90:1, less than 85:1, or less than 80:1. In terms of ranges, the weight ratio of tricyanohexane to the isomer may be from 5:1 to 100:1, e.g., from 5:1 to 95:1, from 5:1 to 90:1, from 5:1 to 85:1, from 5:1 to 80:1, from 8:1 to 100:1, from 8:1 to 95:1, from 8:1 to 90:1, from 8:1 to 85:1, from 8:1 to 80:1, from 10:1 to 100:1, from 10:1 to 95:1, from 10:1 to 90:1, from 10:1 to 85:1, from 10:1 to 80:1, from 15:1 to 100:1, from 15:1 to 95:1, from 15:1 to 90:1, from 15:1 to 85:1, from 15:1 to 80:1, from 20:1 to 100:1, from 20:1 to 95:1, from 20:1 to 90:1, from 20:1 to 85:1, from 20:1 to 80:1, from 25:1 to 100:1, from 25:1 to 95:1, from 25:1 to 90:1, from 25:1 to 85:1, or from 25:1 to 80:1.

The content of the tricyanohexane isomer present in the cyanocarbon composition is not particularly limited and may vary widely. In one embodiment, the cyanocarbon composition comprises from 1 wppb to 10 wt. % tricyanohexane isomer, e.g., 1 wppm to 7 wt. %, 10 wppm to 5 wt. %, 1 wppb to 1 wt. %, from 1 wppb to 0.5 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, from 500 ppm to 2 wt %, from 500 ppm to 1 wt %, from 0.1 wt % to 1 wt %, from 0.15 wt % to 0.9 wt %, from 0.1 wt % to 0.7 wt %, from 0.1 wt % to 0.5 wt %, from 0.25 wt % to 1 wt %, from 0.25 wt % to 0.75 wt %, from 0.1 wt. % to 10 wt. %, from 0.1 wt % to 7 wt %, from 0.1 wt % to 5 wt %, from 0.5 wt % to 10 wt %, from 0.5 wt % to 7 wt %, from 50 ppm to 0.5 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb tricyanohexane isomer, e.g., greater than 10 wppb, greater than 100 wppb, greater than 500 wppb, greater than 1 ppm, greater than 10 ppm, greater than 50 ppm, greater than 0.05 wt %, greater than 0.1 wt %, greater than 0.25 wt %, greater than 0.5 wt %, greater than 1 wt %, or greater than 2 wt %. In terms of upper limits, the cyanocarbon composition may comprise less than 10 wt. % tricyanohexane isomer, e.g., less than 7 wt. %, less than 5 wt. %, less than 4 wt. %, less than 3 wt. %, less than 0.5 wt. %, less than 0.1 wt. %, less than 0.05 wt. %, or less than 0.01 wt. %.

Tetracyano Compounds

In some embodiments, the cyanocarbon composition comprises a tetracyano compound. A tetracyano compound may be any organic compound comprising four cyano, or nitrile, functional groups. The inventors have found that the presence of these tetracyano compounds advantageously provides for may advantageously provide for increased stabilization effect, e.g., increased or improved hygroscopic activity and/or the aforementioned cathode electrolyte layer benefits, by the cyanocarbon composition. For example, the four cyano functional groups of the tetracyano compound may synergistically work with TCH to scavenge water and/or to promote the aforementioned cathode electrolyte layer benefits.

In some embodiments, the tetracyano compound is an organic compound having four cyano, or nitrile, groups on a saturated chain of carbon atoms. For example, in some embodiments, the tetracyano compound is a tetracyanoalkane, e.g., an organic compound having the chemical formula $C_xH_{2x-2}(CN)_4$, wherein x is from 5 to 10. Exemplary tetracyano compounds include tetracyanopentane, tetracyanohexane, tetracyanoheptane, tetracyanooctane, tetracyanononane, and tetracyanodecane, and combinations thereof.

In some embodiments, the tetracyano compound is an organic compound having four cyano, or nitrile, groups on an unsaturated chain of carbon atoms. For example, in some embodiments, the tetracyano compound is tetracyanoalkene, e.g., an organic compound having the chemical formula $C_xH_{2x-4}(CN)_4$, wherein x is from 5 to 10. Exemplary tetracyano compounds include tetracyanopentene, tetracyanohexene, tetracyanoheptene, tetracyanooctene, tetracyanononene, and tetracyanodecene, and combinations thereof.

In terms of chemical structures, the tetracyano compound may have the structure

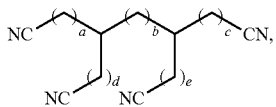

wherein a, b, c, d, and e are independently from 0 to 4, and wherein the sum of a, b, c, d, and e is from 5 to 12.

The content of the tetracyano compound present in the cyanocarbon composition is not particularly limited and may vary widely. In one embodiment, the cyanocarbon composition comprises from 1 wppb to 5 wt. % tetracyano compound, e.g., from 1 wppb to 1 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 0.01 wt % to 5 wt %, from 0.05 ppm to 3 wt %, from 0.05 ppm to 2 wt %, from 0.1 ppm to 1 wt %, from 0.1 ppm to 0.7 wt %, from 100 ppm to 0.5 wt %, from 0.1 wt. % to 1 wt. %, from 0.1 wt. % to 0.8 wt %, from 0.05 wt. % to 1 wt. %, from 0.2 wt. % to 0.6 wt. %, from 200 ppm to 0.5 wt %, 200 ppm to 0.3 wt %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, from 50 ppm to 0.5 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb tetracyano compound, e.g., greater than 10 wppb, greater than 100 wppb, greater than wppb, greater than 1 ppm, greater than 10 ppm, or greater than 50 ppm, greater than 100 wppm, or greater than 200 wppm, greater than 500 wppm, greater than 0.1 wt. %. In terms of upper limits, the cyanocarbon composition may comprise less than 5 wt. % tetracyano compound, e.g., less than 3 wt. %, less than 2 wt. %, less than 0.5 wt. %, less than 0.1 wt. %, less than 0.05 wt. %, or less than 0.01 wt. %.

Cyanoalkenes

In some embodiments, the cyanocarbon composition comprises a cyanoalkene. A cyanoalkene may be any organic compound comprising cyano, or nitrile, functional groups and at least one carbon-carbon double bond. In some embodiments, the cyanoalkene has one carbon-carbon double bond. In some embodiments, the cyanoalkene has at least one carbon-carbon double bond, e.g., at least two, at least three, or at least four. The inventors have found that the presence of these cyanoalkenes may advantageously provide for increased stabilization effect, e.g., increased or improved hygroscopic activity and/or the aforementioned cathode electrolyte layer benefits, by the cyanocarbon composition. For example, the cyano functional group or groups of the cyanoalkene may synergistically work with TCH to scavenge water and/or to promote the aforementioned cathode electrolyte layer benefits.

In some embodiments, the cyanoalkene is a dicyanoalkene, e.g., organic compound having two cyano, or nitrile, groups on an unsaturated chain of carbon atoms. For example, in some embodiments, the cyanoalkene has the chemical formula $C_xH_{2x-2}(CN)_2$, wherein x is from 5 to 10. Exemplary dicyanoalkenes include dicyanopentene, dicyanohexene, dicyanoheptene, dicyanooctene, dicyanononene, and dicyanodecene, and combinations thereof.

In some embodiments, the cyanoalkene is a tricyanoalkene, e.g., organic compound having three cyano, or nitrile, groups on an unsaturated chain of carbon atoms. For example, in some embodiments, the cyanoalkene has the chemical formula $C_xH_{2x-3}(CN)_3$, wherein x is from 5 to 10. Exemplary tricyanoalkenes include tricyanopentene, tricyanohexene, tricyanoheptene, tricyanooctene, tricyanononene, and tricyanodecene, and combinations thereof.

The content of the cyanoalkene present in the cyanocarbon composition is not particularly limited and may vary widely. In one embodiment, the cyanocarbon composition comprises from 1 wppb to 5 wt. % cyanoalkene, e.g., 1 wppb to 3 wt. %, 1 wppb to 1 wt. %, from 1 wppb to 0.5 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, from 500 ppm to 2 wt %, from 500 ppm to 1 wt %, from 0.1 wt % to 1 wt %, from 0.15 wt % to 0.9 wt %, from 0.1 wt % to 0.7 wt %, from 0.1 wt % to 0.5 wt %, from 0.25 wt % to 1 wt %, from 0.25 wt % to 75 wt %, from 50 ppm to 0.5 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb cyanoalkene, e.g., greater than 10 wppb, greater than 100 wppb, greater than 500 wppb, greater than 1 ppm, greater than 10 ppm, greater than 50 ppm, greater than 0.05 wt %, greater than 0.1 wt %, or greater than 0.25 wt %. In terms of upper limits, the cyanocarbon composition may comprise less than 5 wt. % cyanoalkene, e.g., less than 3 wt. %, less than 1 wt. %, less than 0.5 wt. %, less than 0.1 wt. %, less than 0.05 wt. %, or less than 0.01 wt. %.

Cyanoamines

In some embodiments, the cyanocarbon composition comprises a cyanoamine, e.g., a cyanoalkylamine. A cyanoamine may be a primary, secondary, or tertiary amine comprising a cyanoalkyl functional groups. In some embodiments, the cyanoamine has one cyanoalkyl functional group. In some embodiments, the cyanoamine has at least one cyanoalkyl functional group, e.g., at least two, or at least three. The inventors have found that the presence of these cyanoamines may advantageously provide for increased stabilization effect, e.g., increased or improved hygroscopic activity and/or the aforementioned cathode electrolyte layer benefits, by the cyanocarbon composition. For example, the cyano functional group or groups of the cyanoamine may synergistically work with TCH to scavenge water and/or to promote the aforementioned cathode electrolyte layer benefits.

In some embodiments, the cyanoamine is a primary amine having one cyanoalkyl functional group. For example, in some embodiments, the cyanoamine has the chemical formula $NH_2(C_xH_{2x})CN$, wherein x is from 1 to 5. Exemplary primary amines include (cyanomethyl)amine, (cyanoethyl) amine, (cyanopropyl)amine, (cyanobutyl)amine, and (cyanopentyl)amine, and combinations thereof. One particular non-limiting example is tri(2-cyanoethyl)amine.

In some embodiments, the cyanoamine is a secondary amine having two cyanoalkyl functional groups. In some embodiments, the two cyanoalkyl functional groups may be distinct. In some embodiments, the two cyanoalkyl functional groups may be the same. For example, in some embodiments, the cyanoamine has the chemical formula $NH((C_xH_{2x})CN)_2$, wherein x is from 1 to 5. Exemplary secondary amines include bis(cyanomethyl)amine, bis(cyanoethyl)amine, bis(cyanopropyl)amine, bis(cyanobutyl)amine, bis(cyanopentyl)amine, and combinations thereof.

In some embodiments, the cyanoamine is a tertiary amine having three cyanoalkyl functional groups. In some embodiments, the three cyanoalkyl functional groups may be distinct. In some embodiments, the three cyanoalkyl functional groups may be the same. For example, in some embodiments, the cyanoamine has the chemical formula $N((C_xH_{2x})CN)_3$, wherein x is from 1 to 5. Exemplary tertiary amines include tris(cyanomethyl)amine, tris(cyanoethyl)amine, tris(cyanopropyl)amine, tris(cyanobutyl)amine, tris(cyanopentyl)amine, and combinations thereof.

In terms of chemical structures, the cyanoamine may have the chemical structure

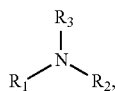

wherein $R_1$ is —H or —$C_xH_{2x}CN$ for x from 1 to 5, $R_2$ is —H or —$C_yH_{2y}CN$ for y from 1 to 5, and $R_3$ is —H or —$C_zH_{2z}CN$ for z from 1 to 5, and wherein at least one of $R_1$, $R_2$, and $R_3$ is not hydrogen.

The content of the cyanoamine present in the cyanocarbon composition is not particularly limited and may vary widely. In one embodiment, the cyanocarbon composition comprises from 1 wppb to 5 wt. % cyanoamine, e.g., from 1 wppb to 1 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 0.01 wt % ppm to 5 wt %, from 0.05 ppm to 3 wt %, from 0.05 ppm to 2 wt %, from 0.1 ppm to 1 wt %, from 0.05 wt % to 0.8 wt %, from 0.05 wt % to 0.6 wt %, from 0.1 wt. % to 0.3 wt %, from 0.01 wt. % to 0.5 wt. %, from 0.1 ppm to 0.7 wt %, from 100 ppm to 0.5 wt %, 200 ppm to 0.5 wt %, 200 ppm to 0.3 wt %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, from 50 ppm to 0.5 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb cyanoamine, e.g., greater than 10 wppb, greater than 100 wppb, greater than wppb, greater than 1 ppm, greater than 10 ppm, or greater than 50 ppm, greater than 100 wppm, or greater than 200 wppm, greater than 500 wppm, greater than 0.1 wt. %. In terms of upper limits, the cyanocarbon composition may comprise less than 5 wt. % cyanoamine, e.g., less than 3 wt. %, less than 2 wt. %, less than 0.5 wt. %, less than 0.1 wt. %, less than 0.05 wt. %, or less than 0.01 wt. %.

Cyanooxime

In some embodiments, the cyanocarbon composition comprises a cyanooxime. A cyanooxime may be any organic compound comprising at least one cyano, or nitrile, functional group and at least one oxime functional group (—C=NOH). In some embodiments, the cyanooxime has one cyano functional group. In some embodiments, the cyanooxime has at least one cyano functional group, e.g., at least two or at least three. The inventors have found that the presence of these cyanooximes may advantageously provide for increased stabilization effect, e.g., increased or improved hygroscopic activity and/or the aforementioned cathode electrolyte layer benefits, by the cyanocarbon composition. For example, the cyano functional group or groups of the cyanooxime may synergistically work with TCH to scavenge water and/or to promote the aforementioned cathode electrolyte layer benefits.

In some embodiments, the oxime functional group is an adloxime group. In some embodiments, the oxime functional group is a ketoxime.

Without being bound by theory, it is believed that the oxime functional group is formed by an oxidation reaction of a cyano functional group. As such, the oxime of the cyanocarbon composition may be formed by converting at least one cyano functional group of any product or coproduct described herein to an oxime functional group. Said another way, the cyanooxime of the cyanocarbon composition may be an oxime of any product or coproduct described herein.

In some embodiments, the cyanooxime is an oxime of tricyanohexane. In some embodiments, the cyanooxime is an oxime of a tetracyano compound. In some embodiments, the cyanooxime is an oxime of a cyanoalkene. In some embodiments, the cyanooxime is an oxime of a cyanoamine. In some embodiments, the cyanooxime is a combination of these.

In terms of chemical structure, in some embodiments, the cyanooxime has the chemical structure:

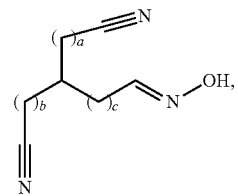

wherein a is 0 to 3, b is 1 to 3, and c is 1 to 4. In some embodiments, the cyanooxime has the chemical structure:

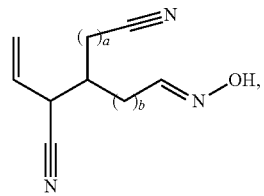

wherein a is from 1 to 3, and b is from 1 to 4.

The content of the cyanooxime present in the cyanocarbon composition is not particularly limited and may vary widely. In one embodiment, the cyanocarbon composition comprises from 1 wppb to 5 wt. % cyanooxime, e.g., from 1 wppb to 1 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 0.01 wt % ppm to 5 wt %, from 0.05 ppm to 3 wt %, from 0.05 ppm to 2 wt %, from 0.1 ppm to 1 wt %, from 0.1 ppm to 0.7 wt %, from 0.05 wt % to 1 wt %, from 0.05 wt % to 0.8 wt %, from 0.1 wt. % to 1 wt %, from 0.2 wt. % to 0.9 wt. %, from 100 ppm to 0.5 wt %, 200 ppm to 0.5 wt %, 200 ppm to 0.3 wt %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, from 50 ppm to 0.5 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb cyanooxime, e.g., greater than 10 wppb, greater than 100 wppb, greater than wppb, greater than 1 ppm, greater than 10 ppm, or greater than 50 ppm, greater than 100 wppm, or greater than 200 wppm, greater than 500 wppm, greater than 0.1 wt. %. In terms of upper limits, the cyanocarbon composition may comprise less than 5 wt. % cyanooxime, e.g., less than 3 wt. %, less than 2 wt. %, less than 0.5 wt. %, less than 0.1 wt. %, less than 0.05 wt. %, or less than 0.01 wt. %.

Cyanoamides

In some embodiments, the cyanocarbon composition comprises a cyanoamide, e.g., a cyanoalkylamide. An amide may be any organic compound comprising at least one cyano, or nitrile, functional group and at least one amide, or carboxamide, functional group (—C=NR$_2$, wherein R is independently hydrogen or an alkyl group). In some embodiments, the cyanoamide has one cyano functional group. In some embodiments, the cyanoalkene has at least one cyano functional group, e.g., at least two or at least three. The amide functional group may be a primary amide, a secondary amide, or a tertiary amide. The inventors have found that the presence of these cyanoamides may advantageously provide for increased stabilization effect, e.g., increased or improved hygroscopic activity and/or the aforementioned cathode electrolyte layer benefits, by the cyanocarbon composition. For example, the cyano functional group or groups of the cyanoamide may synergistically work with TCH to scavenge water and/or to promote the aforementioned cathode electrolyte layer benefits.

Without being bound by theory, it is believed that the amide functional group is formed by a hydrolysis reaction of a cyano functional group. As such, the cyanoamide of the cyanocarbon composition may be formed by converting at least one cyano functional group of any product or coproduct described herein to an amide functional group. Said another way, the cyanoamide of the cyanocarbon composition may be an amide of any product or coproduct described herein.

In some embodiments, the cyanoamide is an amide of tricyanohexane. In some embodiments, the cyanoamide is an amide of a tetracyano compound. In some embodiments, the cyanoamide is an amide of a cyanoalkene. In some embodiments, the cyanoamide is an amide of a cyanoamine. In some embodiments, the cyanoamide is a combination of these.

In terms of chemical structures, in some embodiments, the cyanoamide has the chemical structure:

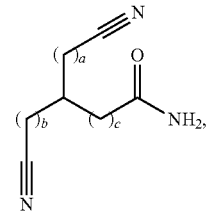

wherein a is 0 to 3, b is 1 to 3, and c is 1 to 4.

The content of the cyanoamide present in the cyanocarbon composition is not particularly limited and may vary widely. In one embodiment, the cyanocarbon composition comprises from 1 wppb to 5 wt. % cyanoamide, e.g., from 1 wppb to 1 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 0.01 wt % ppm to 5 wt %, from 0.05 ppm to 3 wt %, from 0.05 ppm to 2 wt %, from 0.1 ppm to 1 wt %, from 0.1 ppm to 0.7 wt %, from 0.1 wt. % to 0.8 wt %, from 0.05 wt. % to 1 wt. %, from 0.2 wt. % to 0.6 wt. %, from 100 ppm to 0.5 wt %, 200 ppm to 0.5 wt %, 200 ppm to 0.3 wt %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, from 50 ppm to 0.5 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb cyanoamide, e.g., greater than 10 wppb, greater than 100 wppb, greater than wppb, greater than 1 ppm, greater than 10 ppm, or greater than 50 ppm, greater than 100 wppm, or greater than 200 wppm, greater than 500 wppm, greater than 0.1 wt. %. In terms of upper limits, the cyanocarbon composition may comprise less than 5 wt. % cyanoamide, e.g., less than 3 wt. %, less than 2 wt. %, less than 0.5 wt. %, less than 0.1 wt. %, less than 0.05 wt. %, or less than 0.01 wt. %.

Nitriles

In some embodiments, the cyanocarbon composition comprises a nitrile, e.g., adiponitrile. The inventors have found that the presence of these nitirles may advantageously provide for increased stabilization effect, e.g., increased or improved hygroscopic activity and/or the aforementioned cathode electrolyte layer benefits, by the cyanocarbon composition.

The content of the nitrile present in the cyanocarbon composition is not particularly limited and may vary widely. In one embodiment, the cyanocarbon composition comprises from 1 wppb to 5 wt. % nitrile, e.g., 1 wppb to 3 wt. %, 1 wppb to 1 wt. %, from 1 wppb to 0.5 wt. %, from 1 wppb to 0.1 wt. %, from 1 wppb to 0.05 wt. %, from 1 wppb to 0.01 wt. %, 10 wppb to 1 wt. %, from 10 wppb to 0.5 wt. %, from 10 wppb to 0.1 wt. %, from 10 wppb to 0.05 wt. %, from 10 wppb to 0.01 wt. %, 100 wppb to 1 wt. %, from 100 wppb to 0.5 wt. %, from 100 wppb to 0.1 wt. %, from 100 wppb to 0.05 wt. %, from 100 wppb to 0.01 wt. %, 500 wppb to 1 wt. %, from 500 wppb to 0.5 wt. %, from 500 wppb to 0.1 wt. %, from 500 wppb to 0.05 wt. %, from 500 wppb to 0.01 wt. %, 1 ppm to 1 wt. %, from 1 ppm to 0.5 wt. %, from 1 ppm to 0.1 wt. %, from 1 ppm to 0.05 wt. %, from 1 ppm to 0.01 wt. %, 10 ppm to 1 wt. %, from 10 ppm to 0.5 wt. %, from 10 ppm to 0.1 wt. %, from 10 ppm to 0.05 wt. %, from 10 ppm to 0.01 wt. %, 50 ppm to 1 wt. %, from 500 ppm to 2 wt %, from 500 ppm to 1 wt %, from 0.1 wt % to 1 wt %, from 0.15 wt % to 0.9 wt %, from 0.1 wt % to 0.7 wt %, from 0.1 wt % to 0.5 wt %, from 0.25 wt % to 1 wt %, from 0.25 wt % to 75 wt %, from 50 ppm to 0.5 wt. %, from 50 ppm to 0.1 wt. %, from 50 ppm to 0.05 wt. %, or from 50 ppm to 0.01 wt. %. In terms of lower limits the cyanocarbon composition may comprise greater than 1 wppb nitrile, e.g., greater than 10 wppb, greater than 100 wppb, greater than 500 wppb, greater than 1 ppm, greater than 10 ppm, greater than 50 ppm, greater than 0.05 wt %, greater than 0.1 wt %, or greater than 0.25 wt %. In terms of upper limits, the cyanocarbon composition may comprise less than 1 wt. % nitrile, e.g., less than 0.5 wt. %, less than 0.1 wt. %, less than 0.05 wt. %, or less than 0.01 wt. %.

Combinations

The cyanocarbon compositions described herein may comprise tricyanohexane and any combination of above-described coproducts. For example, the cyanocarbon composition may comprise tricyanohexane, an isomer of tricyanohexane, a tetracyanocompound, a cyanoalkene, a cyanoamine, a cyanoxime, or a cyanoamide, or combinations thereof. The compositional ranges and limits disclosed herein for the various coproducts are applicable to combinations of coproducts. In the interest of brevity, those ranges and limits are not repeated here.

In one embodiment, the cyanocarbon composition comprises 1,3 6-tricyanohexane and tricyanohexane isomers. The isomers may be present in the amounts disclosed herein, in particular, the isomers may be present in an amount ranging from 1 ppm to 0.5 wt. %, as shown in the examples.

In one embodiment, the cyanocarbon composition comprises 1,3 6-tricyanohexane and a tetracyano compound having the chemical formula $C_xH_{2x-2}(CN)_4$ wherein x is from 5 to 10. The tetracyano compound may be present in the amounts disclosed herein, in particular, the tetracyano compound may be present in an amount ranging from 1 ppm to 0.5 wt. % as shown in the examples.

In one embodiment, the cyanocarbon composition comprises 1,3 6-tricyanohexane and tricyanoalkenes. The tricyanoalkenes may be present in the amounts disclosed herein, in particular, the tricyanoalkenes may be present in an amount ranging from 1 ppm to 0.5 wt. % as shown in the examples.

In one embodiment, the cyanocarbon composition comprises 1,3 6-tricyanohexane and (cyanoethyl)amine. The (cyanoethyl)amine may be present in the amounts disclosed herein, in particular, the (cyanoethyl)amine may be present in an amount ranging from 1 ppm to 0.5 wt. % as shown in the examples.

In one embodiment, the cyanocarbon composition comprises at least 92 wt. % tricyanohexane, (from 0.1 wt % to 10 wt % of) an isomer of tricyanohexane, wherein the weight ratio of tricyanohexane to the isomer is at least 5:1, and (from 500 ppm to 1 wt % of) adiponitrile.

In one embodiment, the cyanocarbon composition comprises at least 92 wt. % tricyanohexane, (from 0.5 wt % to 7 wt % of) an isomer of tricyanohexane, and (from 0.05 ppm to 2 wt. % of) a tetracyano compound.

In one embodiment, the cyanocarbon composition comprises at least 92 wt. % tricyanohexane, an isomer of tricyanohexane in the disclosed amounts, a tetracyano compound in the disclosed amounts, and (cyanoalkyl)amine in the disclosed amounts, and optionally adiponitrile in the disclosed amounts.

In one embodiment, the cyanocarbon composition comprises at least 92 wt. % tricyanohexane, an isomer of tricyanohexane in the disclosed amounts, a tetracyano compound in the disclosed amounts, and a cyanooxime in the disclosed amounts, and optionally adiponitrile in the disclosed amounts.

In one embodiment, the cyanocarbon composition comprises 1,3 6-tricyanohexane and cyanooximes, e.g., those having the chemical structure

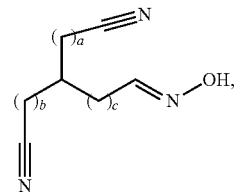

wherein a is 0 to 3, b is 1 to 3, and c is 1 to 4. The cyanooximes may be present in the amounts disclosed herein, in particular, the cyanooximes may be present in an amount ranging from 1 ppm to 0.5 wt. % as shown in the examples.

In one embodiment, the cyanocarbon composition comprises 1,3 6-tricyanohexane and cyano-compounds having the chemical structure

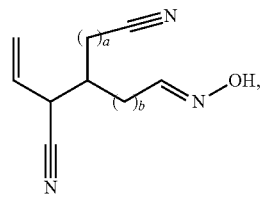

wherein a is from 1 to 3, and b is from 1 to 4. The cyano-compounds may be present in the amounts disclosed herein, in particular, the cyano-compounds may be present in an amount ranging from 1 ppm to 0.5 wt. % as shown in the examples.

In some cases, the coproducts may be formed in situ during the tricyanohexane formation reaction. For example, the coproducts of tricyanohexane may be compounds that are formed in situ during the production of TCH. The coproducts of tricyanohexane may also be compounds that are formed in situ during the purification of tricyanohexane. In some cases, the cyanocarbon composition comprises a mixture of coproducts formed during the tricyanohexane formation reaction and coproducts formed during the tricyanohexane purification.

Method of Making

As noted above, the disclosed cyanocarbon compositions are made by particular processes, and these processes contribute to the unique, synergistic combinations of coproducts (in the disclosed amounts) discussed herein. In particular, it has been discovered that the use of some elecrohydrodimerization process streams, e.g., crude streams and derivatives thereof, may be used to create a TCH-containing stream. Such TCH-containing streams may serve as a feed stream that may then be separated, via specific steps, to yield the disclosed cyanocarbon compositions that comprise valuable amounts of coproducts.

In some cases, TCH-containing feed streams result from the reactions with nitriles, e.g., acrylonitrile and/or adiponitrile, preferably acrylonitrile. These reactions take place upstream of the separation schemes that are described herein. These chemicals, e.g., nitriles, may serve as precursors to the coproducts discussed herein, e.g., those with significant nitrile end-capping. Conventional processes that do not utilize these chemicals result in producing cyanocarbon compositions that have entirely different nitrile footprints, e.g., little or no end-capping. Further, conventional methods of separation and/or purification of TCH-containing feed streams provide little or no guidance relating to the effect of these coproduct concentrations on the final TCH yield or TCH performance. Importantly, the inventors have found that these component concentrations can be effectively manipulated to provide significant efficiency improvements (as discussed previously), which result in a higher purity TCH product along with the surprising performance results.

The process comprises a (first) separating step of separating the adiponitrile process stream to form a first overhead stream and a first bottoms stream. The first overhead stream comprises low-boiling components (lights) and high-boiling components (heavies), and the first bottoms stream comprises high-boiling components. The process further comprises a (second) separating step of separating the first overhead stream, optionally in one or more distillation columns, to form a lights stream comprising low-boiling components, a heavies stream comprising high-boiling components, and a TCH stream comprising TCH and a lower amount of coproducts. Importantly, the residence time of feed streams in the individual operations of the process is minimized, e.g., less than 8 hours. In doing so, decomposition of high-boiling components is advantageously reduced or minimized, which provides for the separation efficiencies mentioned above.

In some cases, some of the coproducts are considered lights and others of the coproducts are considered heavies. By employing the disclosed processes, the synergistic combinations of coproducts (including some heavies and/or some lights) in the aforementioned amounts are achieved.

The process used to form the cyanocarbon compositions of the present disclosure may begin with a specific feed stream containing TCH and impurities. In particular, the feed stream may comprise TCH, high-boiling components, and low boiling components. For example, the feed stream may comprise TCH, and one of more of the coproducts that are discussed herein. In some embodiments, the feed stream may be one or more co-product streams of another industrial chemical production process.

First Separating Step

In some embodiments, the feed stream, e.g., an adiponitrile process stream, is separated in a first separating step to form a first overhead stream comprising low-boiling components (lights) and (optionally lower amounts of) high-boiling components (heavies) and a first bottoms stream comprising high-boiling components and solid impurities. The first separating step, in some cases, removes a significant portion of the heavies (but may leave some) and/or the solid impurities present in the feed stream. The inventors have found that removal of the heavies prior to processing in the second separating step beneficially reduces the decomposition of the high-boiling components and thereby improves the efficiency of the total purification process. Without this initial removal of heavies, additional non-TCH impurities are formed, which must then be separated, creating additional operations and uncertainties. Furthermore, the inventors have also found that early removal of the heavies and the solid impurities reduces fouling of distillation columns, which improves downstream efficiency and eliminates or reduces the need for subsequent separation operations. The residence time of the feed stream in the first separation step may be a short residence time as discussed herein.

In some embodiments, the first separating step includes separation in a flasher, e.g., a flash evaporator. In these embodiments, the feed stream is evaporated and separated into the first overhead stream and the first bottoms stream. Various flashers are known to those of ordinary skill in the art, and any suitable flasher may be employed as long as the separation described herein is achieved. In some embodiments, the separation in the flasher may be caused by reducing the pressure, e.g., an adiabatic flash, without heating the feed stream. In other embodiments, the separation in the flasher may be caused by raising the temperature of the feed stream without changing the pressure. In still other embodiments, the separation in the flasher may be caused by reducing the pressure while heating the feed stream. In some embodiments, the first separating step is achieved via a wiped film evaporator (WFE).

In some embodiments, the first separating step includes separating the feed stream in a flash evaporator at reduced pressure, e.g., under a vacuum. In some embodiments, the pressure in the flash evaporator is reduced to less than 25 torr, e.g., less than 20 torr, less than 10 torr, or less than 5 torr.

In some embodiments, the flash vessel of the first separating step is kept at a constant temperature. In some embodiments, the temperature of the flash vessel may be from 175° C. to 235° C., e.g., from 180° C. to 230° C., from 185° C. to 225° C., or from 190° C. to 220° C.

The first bottoms stream comprises high-boiling components (heavies). Examples of heavies that may be present in the first bottoms stream include isomers of tricyanohexane, tri(2-cyanoethyl)amine, other coproducts, and combinations thereof. In one embodiment, the first separation step includes in a flasher, and the first bottoms stream comprises isomers of tricyanohexane and tri(2-cyanoethyl)amine.

The first bottoms stream also comprises solid impurities. In one embodiment, the first separation step removes all (i.e., 100%) of the solid impurities from the feed stream. Said another way, in this embodiment, the first overhead stream comprises 0 wt. % solid impurities. In other embodiments, the first separation step may remove less than 100% of the solid impurities, e.g., less than 99.9%, less than 99%, or less than 98%.

The first overhead stream comprises heavies and lights. In some cases, some of the coproduct are lights and others of the coproducts are heavies. The first overhead stream also comprises TCH. The first separation step, in some cases, does not remove all of the heavies from the feed stream, and some heavies may remain in the first overhead stream (along with some lights). In some embodiments, the coproduct heavies in the first overhead stream contribute to the presence of the coproduct heavies in the resultant cyanocarbon compositions. Stated another way, the coproducts that are present in the cyanocarbon compositions (in the specific amounts mentioned herein) may be present, at least in part, in the first overhead stream.

In some embodiments, the first overhead stream comprises TCH in a higher concentration than that of the feed stream. In one embodiment, the first overhead stream comprises TCH in an amount ranging from 60 wt. % to 98 wt. %, e.g., from 60 wt. % to 97 wt. %, from 60 wt. % to 96 wt. %, from 60 wt. % to 95 wt. %, from 65 wt. % to 98 wt. %, from 65 wt. % to 97 wt. %, from 65 wt. % to 96 wt. %, from 65 wt. % to 95 wt. %, from 70 wt. % to 98 wt. %, from 70 wt. % to 97 wt. %, from 70 wt. % to 96 wt. %, from 70 wt. % to 95 wt. %, from 75 wt. % to 98 wt. %, from 75 wt. % to 97 wt. %, from 75 wt. % to 96 wt. %, or from 75 wt. % to 95 wt. %. In terms of upper limits, the first overhead stream may comprise less than 98 wt. % TCH, e.g., less than 97 wt. %, less than 96 wt. %, or less than 95 wt. %. In terms of lower limits, the first overhead stream may comprise greater than 60 wt. % TCH, e.g., greater than 65 wt. %, greater than 70 wt. %, or greater than 75 wt. %.

In one embodiment, the first overhead stream comprises lights in an amount ranging from 0 wt. % to 30 wt. %, e.g., from 0 wt. % to 25 wt. %, from 0 wt. %, to 20 wt. %, from 0 wt. % to 15 wt. %, from 0 wt. % to 10 wt. %, from 1 wt. % to 30 wt. %, from 1 wt. % to 25 wt. %, from 1 wt. %, to 20 wt. %, from 1 wt. % to 15 wt. %, from 1 wt. % to 10 wt. %, from 2 wt. % to 30 wt. %, from 2 wt. % to 25 wt. %, from 2 wt. %, to 20 wt. %, from 2 wt. % to 15 wt. %, from 2 wt. % to 10 wt. %, from 3 wt. % to 30 wt. %, from 3 wt. % to 25 wt. %, from 3 wt. %, to 20 wt. %, from 3 wt. % to 15 wt. %, from 3 wt. % to 10 wt. %, from 4 wt. % to 30 wt. %, from 4 wt. % to 25 wt. %, from 4 wt. %, to 20 wt. %, from 4 wt. % to 15 wt. %, from 4 wt. % to 10 wt. %, from 5 wt. % to 30 wt. %, from 5 wt. % to 25 wt. %, from 5 wt. %, to 20 wt. %, from 5 wt. % to 15 wt. %, or from 5 wt. % to 10 wt. %. In terms of upper limits, the first overhead stream may comprise less than 30 wt. % lights, e.g., less than 25 wt. %, less than 20 wt. %, less than 15 wt. %, or less than 10 wt. %. In terms of lower limits, the first overhead stream may comprise greater than 0 wt. % lights, e.g., greater than 1 wt. %, greater than 2 wt. %, greater than 3 wt. %, greater than 4 wt. %, or greater than 5 wt. %.

In one embodiment, the first overhead stream comprises heavies in an amount ranging from 0 wt. % to 20 wt. %, e.g., from 0 wt. % to 15 wt. %, from 0 wt. % to 10 wt. %, from 0 wt. % to 8 wt. %, from 0 wt. % to 5 wt. %, from 0.5 wt. % to 20 wt. %, from 0.5 wt. % to 15 wt. %, from 0.5 wt. % to 10 wt. %, from 0.5 wt. % to 8 wt. %, from 0.5 wt. % to 5 wt. %, from 1 wt. % to 20 wt. %, from 1 wt. % to 15 wt. %, from 1 wt. % to 10 wt. %, from 1 wt. % to 8 wt. %, from 1 wt. % to 5 wt. %, from 1.5 wt. % to 20 wt. %, from 1.5 wt. % to 15 wt. %, from 1.5 wt. % to 10 wt. %, from 1.5 wt. % to 8 wt. %, from 1.5 wt. % to 5 wt. %, from 2 wt. % to 20 wt. %, from 2 wt. % to 15 wt. %, from 2 wt. % to 10 wt. %, from 2 wt. % to 8 wt. %, from 2 wt. % to 5 wt. %, from 2.5 wt. % to 20 wt. %, from 2.5 wt. % to 15 wt. %, from 2.5 wt. % to 10 wt. %, from 2.5 wt. % to 8 wt. %, or from 2.5 wt. % to 5 wt. %. In terms of upper limits, the first overhead stream may comprise less than 20 wt. % heavies, e.g., less than 15 wt. %, less than 10 wt. %, less than 8 wt. %, or less than 5 wt. %, In terms of lower limits, the first overhead stream may comprise greater than 0 wt. % heavies, e.g., greater than 0.5 wt. %, greater than 1 wt. %, greater than 1.5 wt. %, greater than 2 wt. %, or greater than 2.5 wt. %.

In some cases, the first separation step removes a significant portion of the heavies from the feed stream. In some embodiments, the first overhead stream comprises less than 70% of the heavies present in the feed stream, e.g., less than 65%, less than 60%, less than 55%, or less than 50%.

Second Separating Step

As noted above, the first overhead stream is subjected to further purification in the second separating step. In particular, the first overhead stream is separated in a second separation step to form a lights stream comprising lights (low-boiling components), a heavies stream comprising heavies (high-boiling components), and a TCH stream comprising TCH. The first separating step, in some cases, removes a significant portion (if not all) of the low-boiling components and high-boiling components present in the first overhead stream. The residence time of the feed stream in the second separation step may be a short residence time as discussed herein.

The lights stream comprises lights, e.g., the above-described impurities having relatively low boiling points. In one embodiment, the lights stream comprises low-boiling components in an amount ranging from 10 wt. % to 60 wt. %, e.g., from 10 wt. % to 55 wt. %, from 10 wt. % to 45 wt. %, from 10 wt. % to 40 wt. %, from 10 wt. % to 35 wt. %, from 15 wt. %, to 60 wt. %, from 15 wt. % to 55 wt. %, from 15 wt. % to 45 wt. %, from 15 wt. % to 40 wt. %, from 15 wt. % to 35 wt. %, from 20 wt. %, to 60 wt. %, from 20 wt. % to 55 wt. %, from 20 wt. % to 45 wt. %, from 20 wt. % to 40 wt. %, from 20 wt. % to 35 wt. %, from 25 wt. %, to 60 wt. %, from 25 wt. % to 55 wt. %, from 25 wt. % to 45 wt. %, from 25 wt. % to 40 wt. %, from 25 wt. % to 35 wt. %, from 30 wt. %, to 60 wt. %, from 30 wt. % to 55 wt. %, from 30 wt. % to 45 wt. %, from 30 wt. % to 40 wt. %, or from 30 wt. % to 35 wt. %. In some embodiments, the light stream comprises from 10 wt. % to 30 wt. % low-boiling components, e.g., from 10 wt. % to 25 wt. %, from 10 wt. % to 20 wt. %, or from 10 wt. % to 15 wt. %. In terms of upper limits, the lights stream may comprise less than 60 wt. % low-boiling components, e.g., less than 55 wt. %, less than 45 wt. %, less than 40 wt. %, or less than 35 wt. %. In terms of lower limits, the lights stream may comprise greater than 10 wt. % low-boiling components, e.g., greater than 15 wt. %, greater than 20 wt. %, greater than 25 wt. %, or greater than 30 wt. %.

The heavies stream comprises high-boiling components (heavies). In one embodiment, the heavies stream comprises high-boiling components in an amount ranging from 5 wt. % to 50 wt. %, e.g., from 5 wt. % to 45 wt. %, from 5 wt. % to 40 wt. %, from 5 wt. % to 35 wt. %, from 5 wt. % to 30 wt. %, from 8 wt. % to 50 wt. %, from 8 wt. % to 45 wt. %, from 8 wt. % to 40 wt. %, from 8 wt. % to 35 wt. %, from 8 wt. % to 30 wt. %, from 10 wt. % to 50 wt. %, from 10 wt. % to 45 wt. %, from 10 wt. % to 40 wt. %, from 10 wt. % to 35 wt. %, from 10 wt. % to 30 wt. %, from 12 wt. % to 50 wt. %, from 12 wt. % to 45 wt. %, from 12 wt. % to 40 wt. %, from 12 wt. % to 35 wt. %, from 12 wt. % to 30 wt. %, from 15 wt. % to 50 wt. %, from 15 wt. % to 45 wt. %, from 15 wt. % to 40 wt. %, from 15 wt. % to 35 wt. %, or from 15 wt. % to 30 wt. %. In some embodiments, the heave stream comprises from 5 wt. % to 30 wt. % high-boiling components, e.g. from 5 wt. % to 25 wt. %, from 5 wt. % to 20 wt. %, or from 5 wt. % to 15 wt. %. In terms of upper limits, the heavies stream may comprise less than 50 wt. % high-boiling components, e.g., less than 45 wt. %, less than 40 wt. %, less than 35 wt. %, or less than 30 wt. %. In terms of lower limits, the heavies stream may comprise greater than 5 wt. % high-boiling components, e.g., greater than 8 wt. %, greater than 10 wt. %, greater than 12 wt. %, or greater than 15 wt. %.

The TCH stream comprises TCH. In one embodiment, the TCH stream comprises TCH in an amount ranging from 90 wt. % to 100 wt. %, e.g., from 90 wt. % to 99.9 wt. %, from 90 wt. % to 99 wt. %, from 90 wt. % to 98 wt. %, from 92.5 wt. % to 100 wt. %, from 92.5 wt. % to 99.9 wt. %, from 92.5 wt. % to 99 wt. %, from 92.5 to 98 wt. %, from 95 wt. % to 100 wt. %, from 95 wt. % to 99.9 wt. %, from 95 wt. % to 99 wt. %, from 95 to 98 wt. %, from 97.5 wt. % to 100 wt. %, from 97.5 wt. % to 99.9 wt. %, from 97.5 to 99 wt. %, or from 97.5 to 98 wt. %. In terms of upper limits, the TCH stream may comprise less than 100 wt. % TCH, e.g., less than 99.9 wt. % less than 99 wt. %, or less than 98 wt. %. In terms of lower limits, the TCH stream may comprise greater than 90 wt. %, e.g., greater than 92.5 wt. %, greater than 95 wt. %, or greater than 97.5 wt. %. Conventional processes have been unable to achieve such high TCH purity levels.

These TCH purification methods produce a high-purity TCH stream, e.g., a cyanocarbon composition, as discussed herein. Nevertheless, the TCH stream may still comprise some coproducts. Generally, these coproducts are present in relatively small amounts, e.g., those disclosed herein. As discussed previously, these TCH/coproduct cyanocarbon compositions demonstrate the synergistic performance features discussed herein.

Coproducts present in the TCH stream are typically the aforementioned nitrile compounds and may also optionally have amide and/or oxime functionalities. Examples of impurities that may be present in the TCH stream include adiponitrile, di(2-cyanotethyl) amine, di(2-cyanoethyl) propylamine, tri(2-cyanoethyl) amine, cyanovaleramide, other coproducts disclosed herein, or combinations thereof.

The TCH stream may also comprise small amounts of other high-boiling and/or low-boiling impurities. Unlike various other impurities that present in lower-purity, conventional TCH products, these impurities are typically nitrile compounds. As such, they may improve the ultimate performance of the TCH product. Furthermore, the presence of impurities in the TCH stream may provide a fingerprint for the disclosed purification methods, e.g., a means of identifying a TCH product formed by an embodiment of the present disclosure.

In one embodiment, the TCH stream comprises impurities in an amount ranging from 0 wt. % to 10 wt. %, e.g., from 0 wt. % to 7.5 wt. %, from 0 wt. % to 5 wt. %, from 0 wt. % to 2.5 wt. %, from 0.1 wt. % to 10 wt. %, from 0.1 wt. % to 7.5 wt. %, from 0.1 wt. % to 5 wt. %, from 0.1 wt. % to 2.5 wt. %, from 1 wt. % to 10 wt. %, from 1 wt. % to 7.5 wt. %, from 1 wt. % to 5 wt. %, from 1 wt. % to 2.5 wt. %, from 2 wt. % to 10 wt. %, from 2 wt. % to 7.5 wt. %, from 2 wt. % to 5 wt. %, or from 2 wt. % to 2.5 wt. %. In some embodiments, the TCH stream comprises from 0 wt. % to 2.5 wt. % impurities, e.g., from 0 wt. % to 2 wt. %, from 0 wt. % to 1.5 wt. %, from 0 wt. % to 1 wt. %, from 0.5 wt. % to 2.5 wt. %, from 0.5 wt. % to 2 wt. %, from 0 wt. % to 1.5 wt. %, or from 0 wt. % to 1 wt. %. In terms of upper limits, the TCH stream may comprise less than 10 wt. % impurities, e.g., less than 7.5 wt. %, less than 5 wt. %, or less than 2.5 wt. %. In terms of lower limits, the TCH stream may comprise greater than 0 wt. % impurities, e.g., greater than 0.1 wt. %, greater than 1 wt. %, or greater than 2 wt. %.

In one embodiment, the TCH stream comprises from 0 wt. % to 0.05 wt. % adiponitrile, from 0 wt. % to 0.1 wt. % di(2-cyanoethyl) amine, from 0 wt. % to 0.05 wt. % cyanovaleramide, and from 0 wt. % to 0.05 wt. % tri(2-cyanoethyl) amine. In one embodiment, the TCH stream comprises from 0 wt. % to 0.01 wt. % adiponitrile, from 0 wt. % to 0.01 wt. % low-boiling components, and from 0 wt. % to 1 wt. % high-boiling components.

The second separating step may include separation of the first overheard stream in one or more distillation columns and/or in one or more flash evaporators. The structure of the one or more distillation columns may vary widely. Various distillation columns are known to those of ordinary skill in the art, and any suitable column may be employed in the second separation step as long as the separation described herein is achieved. For example, the distillation column may comprise any suitable separation device or combination of separation devices. For example, the distillation column may comprise a column, e.g., a standard distillation column, an extractive distillation column and/or an azeotropic distillation column. Similarly, as noted above, various flashers are known to those of ordinary skill in the art, and any suitable flasher may be employed in the second separation step as long as the separation described herein is achieved. For example, the flasher may comprise an adiabatic flash evapaorator, a heated flash evaporator, or a wipe film evaporator, or combinations thereof.

For example, in FIG. 1, the second step is achieved via the combination of columns 105 and 108. Stream 106 represents the lights stream comprising lights (low-boiling components), stream 109 represents the heavies stream comprising heavies (high-boiling components), and stream 110 represents the TCH stream comprising TCH and the aforementioned coproducts.

Embodiments of the second separating step may include any combination of one or more distillation columns and/or one or more flashers, and a person of skill in the art would appreciate and understand how to combine these separators to achieve a separation that forms a lights stream, a heavies stream, and a TCH stream.

In some embodiments, the second separating step includes separation of the first overhead stream in two distillation columns. For example, the first overhead stream may be distilled in a first distillation column to form a second overhead stream, a second bottoms stream, and/or a side draw. The second bottoms stream and/or the side draw may then be distilled in a second distillation column to produce the TCH stream.

In some embodiments, the second separating step includes separation of the first overhead stream in three distillation columns. For example, the first overhead stream may be distilled in a first distillation column to form a second overhead stream, a second bottoms stream, and/or a side draw. The second bottoms stream and/or the side draw may then be distilled in a second distillation column to produce a third overhead stream and a third bottoms stream. The third overhead stream may then be distilled in a third distillation column to produce the TCH stream.

Configurations

FIGS. 1-5 show schematic overviews of several configurations of the TCH purification processes disclosed herein.

FIG. 1 shows one embodiment of the TCH purification process 100. In this embodiment, an adiponitrile process stream 101 is separated in a flash evaporator 102 to form a first overhead stream 103 and a first bottoms stream 104. The first overhead stream 103 is then separated in a first distillation column 105 to form a lights stream as a second overhead stream 106 and a second bottoms stream 107. The second bottoms stream is then separated in a second distillation column 108 to form a heavies stream as a third bottoms stream 109 and a TCH stream as a third overhead stream 110. This embodiment also features an optional recycle step 111, whereby a portion of the third bottoms stream 109 is recycled to the first overhead stream 103 and/or the second bottoms stream 107.

Figure 2:
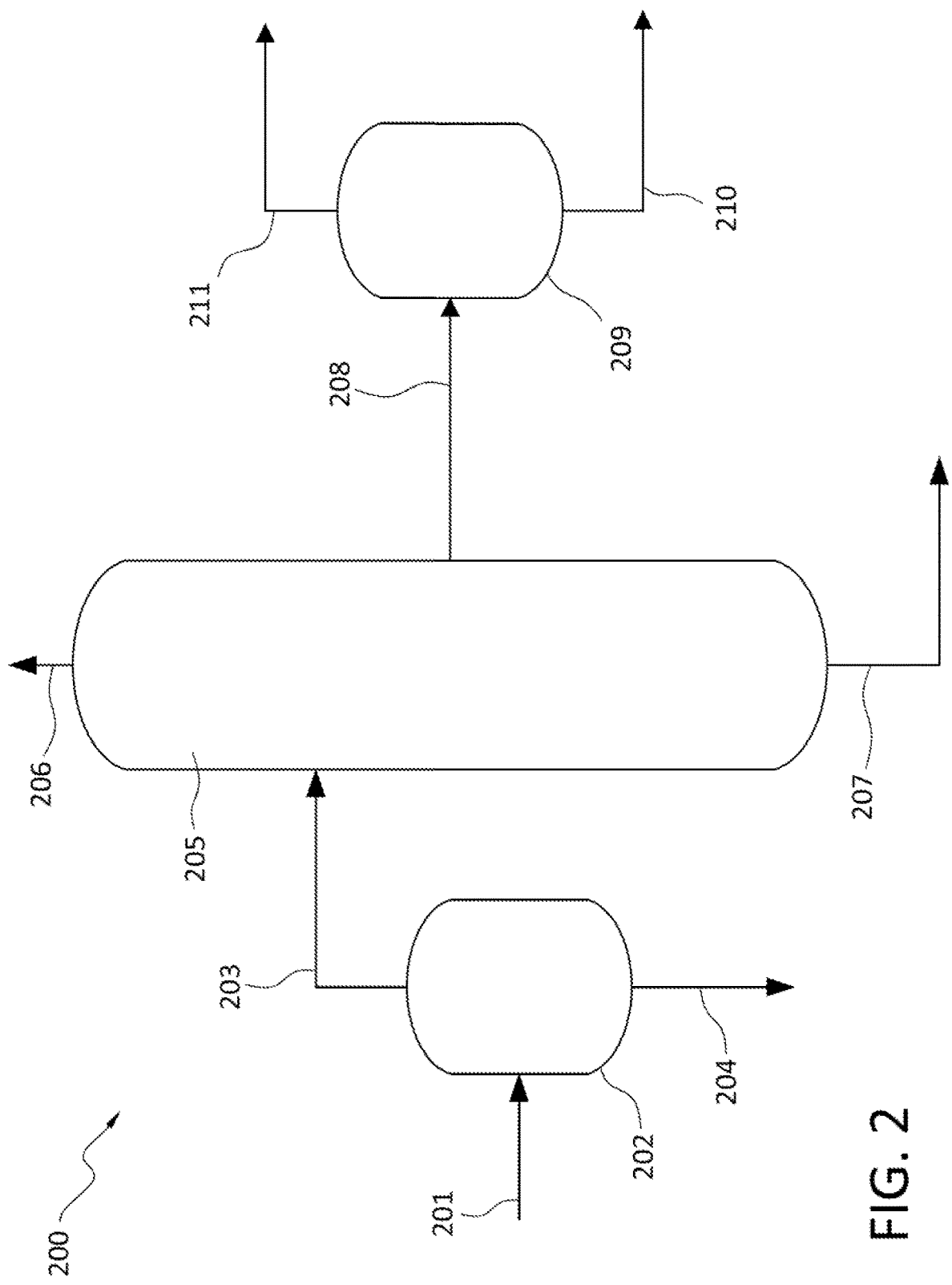
FIG. 2 depicts a schematic overview of another embodiment of the process of purifying TCH.

FIG. 2 shows another embodiment of the TCH purification process 200. In this embodiment, an adiponitrile process stream 201 is separated in a flash evaporator 202 to form a first overhead stream 203 and a first bottoms stream 204. The first overhead stream 203 is then separated in a first distillation column 205 to form a lights stream as a second overhead stream 206, a second bottoms stream 207, and a side draw 208. The side draw 208 is then separated in separated in a flasher 209 to form a TCH stream as a third bottoms stream 210 and a third overhead stream 211.

Figure 3:
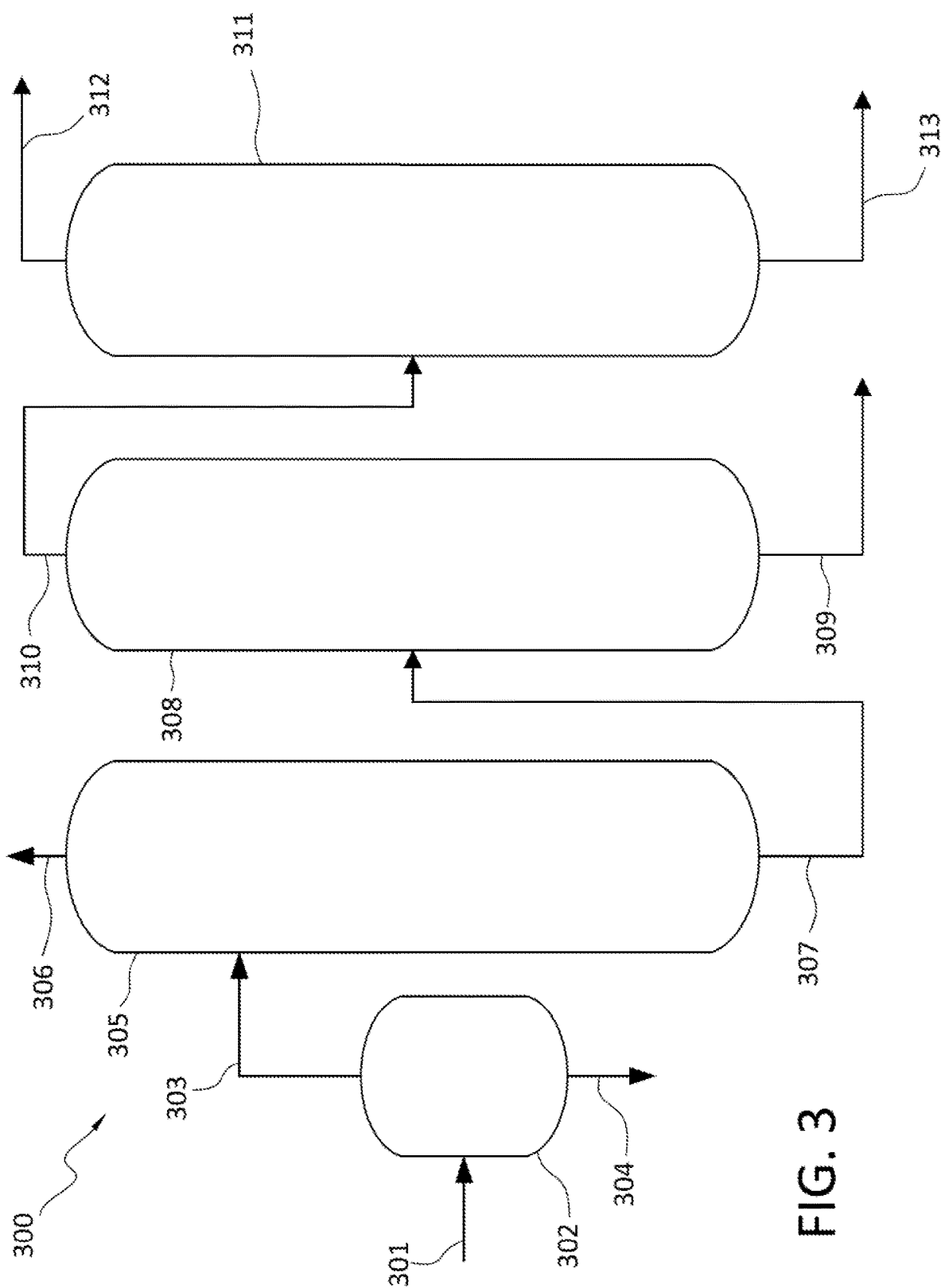
FIG. 3 depicts a schematic overview of another embodiment of the process of purifying TCH.

FIG. 3 shows another embodiment of the TCH purification process 300. In this embodiment, an adiponitrile process stream 301 is separated in a flash evaporator 302 to form a first overhead stream 303 and a first bottoms stream 304. The first overhead stream 303 is then separated in a first distillation column 305 to form a lights stream as a second overhead stream 306 and a second bottoms stream 307. The second bottoms stream 307 is then separated in a second distillation column 308 to form a heavies stream as a third bottoms stream 309 and a third overhead, or distillate, stream 310. The third overhead stream 310 is then separated in a third distillation column 311 to form a fourth overhead stream 312 and a TCH stream as a fourth bottoms stream 313.

Figure 4:
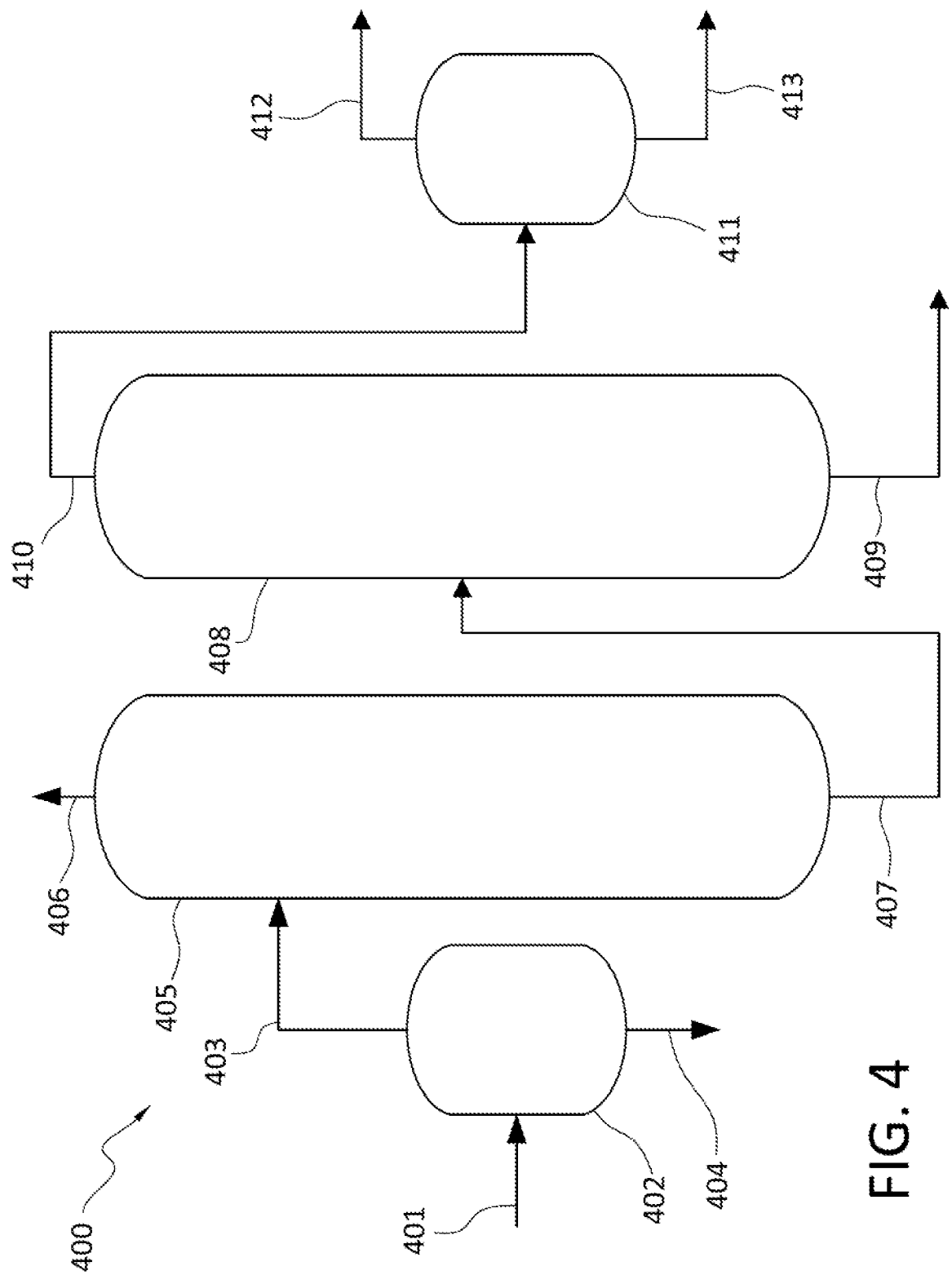
FIG. 4 depicts a schematic overview of another embodiment of the process of purifying TCH.

FIG. 4 shows another embodiment of the TCH purification process 400. In this embodiment, an adiponitrile process stream 401 is separated in a flash evaporator 402 to form a first overhead stream 403 and a first bottoms stream 404. The first overhead stream 403 is then separated in a first distillation column 405 to form a lights stream as a second overhead stream 406 and a second bottoms stream 407. The second bottoms stream 407 is then separated in a second distillation column 408 to form a heavies stream as a third bottoms stream 409 and a third overhead, or distillate, stream 410. The third overhead stream 410 is then separated in a flasher 411 to form a fourth overhead stream 412 and a TCH stream as a fourth bottoms stream 413.

Figure 5:
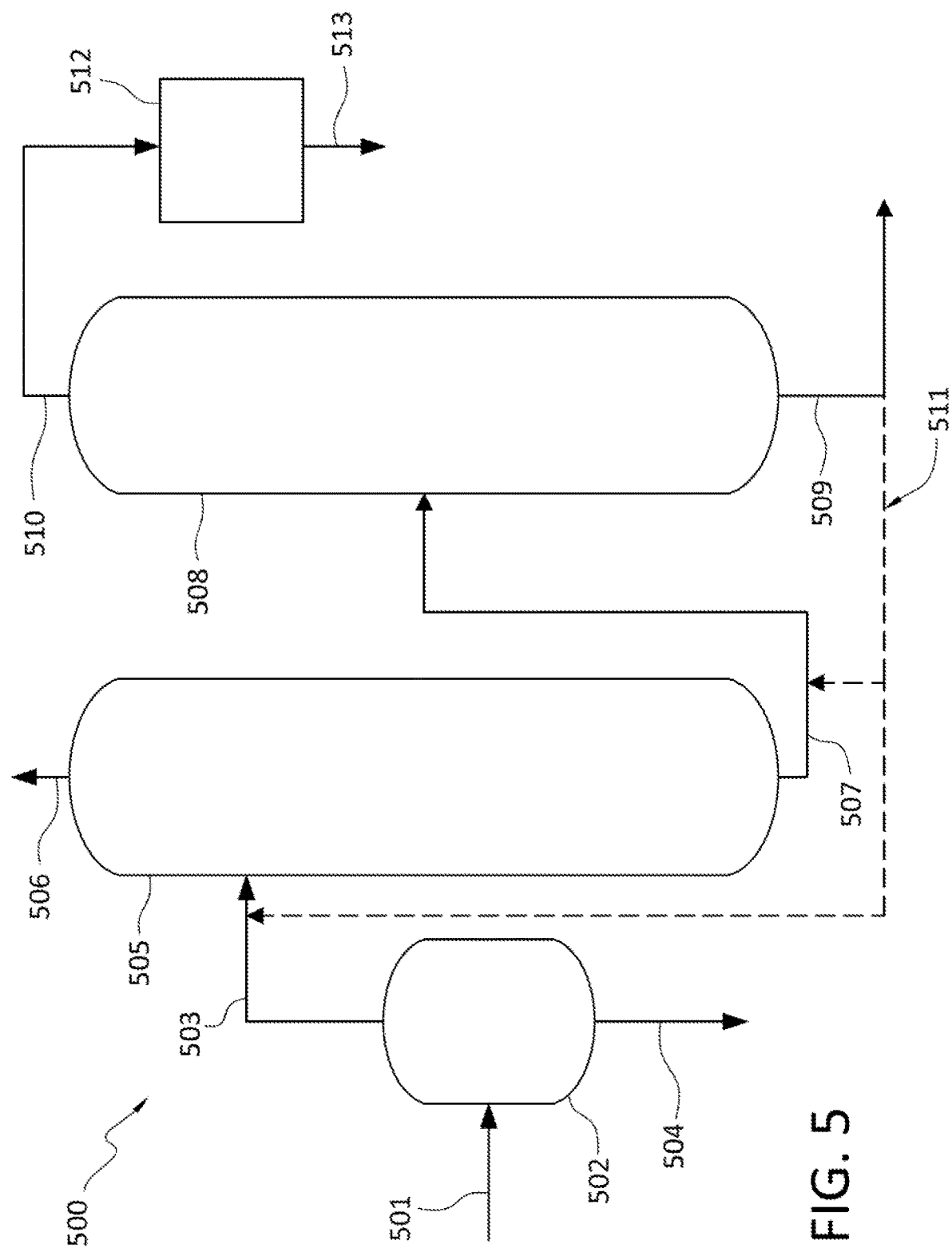
FIG. 5 depicts a schematic overview of another embodiment of the process of purifying TCH.

FIG. 5 shows another embodiment of the TCH purification process 500. In this embodiment, an adiponitrile process stream 501 is separated in a flash evaporator 502 to form a first overhead stream 503 and a first bottoms stream 504. The first overhead stream 503 is then separated in a first distillation column 505 to form a lights stream as a second overhead stream 506 and a second bottoms stream 507. The second bottoms stream 507 is then separated in a second distillation column 508 to form a heavies stream as a third bottoms stream 509 and a TCH stream as a third overhead stream 510. This embodiment also features an optional recycle step 511, whereby a portion of the third bottoms stream 509 is recycled to the first overhead stream 503 and/or the second bottoms stream 507. This embodiment also features a treating step 512, whereby the TCH stream 510 is subjected to further treatment to yield a purified TCH stream 513.

EXAMPLES

Examples of cyanocarbon compositions were prepared by separating a feed stream that was a derivative of an EHD reaction process stream. The feed stream was separated using the scheme detailed in FIG. 1 (employing a wiped film evaporator as evaporator 102).

The cyanocarbon compositions of were analyzed via gas chromatograph, and the component concentration ranges were estimated based on the chromatogram. The results are shown in Tables 1A and 1B.

TABLE 1A

| Cyananocarbon Compositions of Exs. 1-5 | | | | | |
| --- | --- | --- | --- | --- | --- |
| Component | Ex. 1 | Ex. 2 | Ex. 3 | Ex. 4 | Ex. 5 |
| | Concentration, ppm or wt % | | | | |
| 1,3,6 TCH | | | 90+ wt % | | |
| TCH Isomers (e.g., trimers) | 0.1 wt. % - 10 wt. % | | | | |
| Tetracyano compounds | | 0.01 wt. % ppm - 5 wt. % | | | |
| (di/tri)cyanoalkenes | | | 500 ppm to 2 wt % | | |
| (Cyanoalkyl)amine | | | | 0.01 wt. % ppm - 5 wt. % | |
| Cyanooxime | | | | | 0.01 wt. % ppm - 5 wt. % |

TABLE 1B

| Cyananocarbon Compositions of Exs. 6-8 | | | |
| --- | --- | --- | --- |
| Component | Ex. 6 | Ex. 7 | Ex. 8 |
| 1,3,6 TCH | | 90+ wt % | |
| Hexanedinitrile 1 | 0.01 wt. % ppm - 5 wt. % | | |
| 3,3'-iminobis-propanenitrile | | 1 ppm to 0.1 wt. % | |
| cyanoalkylamide 3 | | | 0.01 wt. % ppm - 5 wt. % |

Beneficially the cyanocarbon compositions of Exs. 1-8, were utilized to produce batteries. Advantageously, the combination of the coproducts and the TCH was found to interact with the electrodes (cathodes) during the formation step to create a robust cathode electrolyte interface layer, e.g., degradation was significantly reduced during operation. Further, Exs. 1-8 were found to be more hygroscopic than conventional cyanocarbon compositions that did not comprise the aforementioned coproducts. In addition, Exs. 1-8 were found to be particularly useful as compositional indicators—these were effective as analytical tools, e.g., chemical fingerprints, that improved analysis of the cyanocarbon compositions, when they were employed in production applications, e.g., electrolyte solutions.

EMBODIMENTS

As used below, any reference to a series of embodiments is to be understood as a reference to each of those embodiments disjunctively (e.g., "Embodiments 1-4" is to be understood as "Embodiments 1, 2, 3, or 4").

Embodiment 1 is a cyanocarbon composition comprising: tricyanohexane; and an isomer of tricyanohexane; wherein the weight ratio of tricyanohexane to the isomer is at least 5:1.

Embodiment 2 is a cyanocarbon composition comprising: at least 85 wt. % tricyanohexane; and 1 wppb to 1 wt. % a tetracyano compound having the chemical formula $C_xH_{2x-2}(CN)_4$; wherein x is from 5 to 10.

Embodiment 3 is a cyanocarbon composition comprising: at least 85 wt. % tricyanohexane; and 1 wppb to 1 wt % a tricyanoalkene.

Embodiment 4 is a cyanocarbon composition comprising: at least 85 wt. % tricyanohexane; and 1 wppb to 1 wt. % (cyanoethyl)amine.

Embodiment 5 is a cyanocarbon composition comprising: at least 85 wt. % tricyanohexane; 1 wppb to 1 wt. % a cyanooxime having the chemical structure

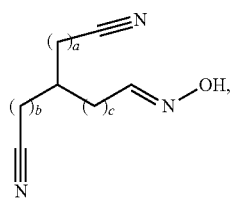

wherein a is 0 to 3, b is 1 to 3, and c is 1 to 4.

Embodiment 6 is a cyanocarbon composition comprising: at least 85 wt. % tricyanohexane; 1 wppb to 1 wt. % a cyano-compound having the chemical structure

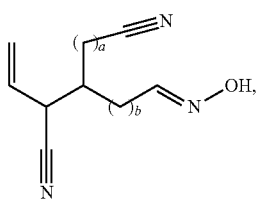

wherein a is from 1 to 3, and b is from to.

Embodiment 7 is a cyanocarbon composition comprising: at least 85 wt. % tricyanohexane; a first cyano-compound having the chemical formula $C_xH_{2x-2}(CN)_4$; a second cyano-compound having the chemical formula $C6H11(CN)_2(CNOH)$; and a third cyano-compound having the chemical formula $C_xH_{2x-3}(CN)_2(CNOH)$ wherein x is independently from 5 to 10; wherein the weight ratio of the first cyano-compound to the second cyano-compound is less than 1; wherein the weight ratio of the second cyano-compound to the second cyano-compound is greater than 1.

Embodiment 8 is a cyanocarbon composition, comprising: tricyanohexane a tricyanohexane coproduct having a molecular weight ranging from 145 to 180 amu.

Embodiment 9 is a cyanocarbon composition, comprising: tricyanohexane; and an in situ-formed coproduct comprising an isomer of tricyanohexane, a cyanoethylamine, an oxime of tricyanohexane, an amide of tricyanohexane, a tetracyanoalkane, or combinations thereof. In some aspects, the cyanocarbon composition comprises at least 92 wt. % tricyanohexane, preferably at least 95 wt % tricyanohexane.

Embodiment 11 is the embodiment of any of the preceding embodiments, wherein the isomer of tricyanohexane comprises 1,2,3-tricyanohexane, 1,2,6-tricyanohexane, 1,3,4-tricyanohexane, 1,3,5-tricyanohexane, 1,3,6-tricyanohexane, 1,4,5-tricyanohexane, or 2,3,5-tricyanohexane, or combinations thereof.

Embodiment 12 is the embodiment of any of the preceding embodiments, wherein the cyanoethylamine comprises tri-(cyanoethyl)amine.

Embodiment 13 is the embodiment of any of the preceding embodiments, wherein the cyanocarbon composition comprises less than 0.1 wt. % isomer of tricyanohexane.

Embodiment 14 is the embodiment of any of the preceding embodiments, wherein the cyanocarbon composition comprises less than 0.1 wt. % tetracyanoalkane.

Embodiment 15 is the embodiment of any of the preceding embodiments, wherein the cyanocarbon composition comprises less than 0.1 wt. % tricyanoalkene.

Embodiment 16 is the embodiment of any of the preceding embodiments, wherein the cyanocarbon composition comprises less than 0.1 wt. % tri-(cyanoethyl)amine.

Embodiment 17 is the embodiment of any of the preceding embodiments, wherein the cyanocarbon composition comprises less than 0.1 wt. % cyanooxime.

Embodiment 18 is the embodiment of any of the preceding embodiments, wherein the cyanocarbon composition comprises less than 0.1 wt. % tricyanohexane coproduct having a molecular weight ranging from 145 to 180 amu.

Embodiment 19 is the embodiment of any of the preceding embodiments, wherein the cyanocarbon composition comprises less than 0.1 wt. % in-situ formed coproduct.

Embodiment 20 is a cyanocarbon composition comprising tricyanohexane; and from 1 wppb to 10 wt. % of tricyanohexane coproduct.

Embodiment 21 is an embodiment of any of the preceding embodiments, wherein the tricyanohexane coproduct comprises an isomer of tricyanohexane.

Embodiment 22 is an embodiment of any of the preceding embodiments, wherein the weight ratio of tricyanohexane to the isomer is at least 5:1.

Embodiment 23 is an embodiment of any of the preceding embodiments, wherein the isomer of tricyanohexane comprises 1,2,3-tricyanohexane, 1,2,6-tricyanohexane, 1,3,4-tricyanohexane, 1,3,5-tricyanohexane, 1,3,6-tricyanohexane, 1,4,5-tricyanohexane, or 2,3,5-tricyanohexane, or combinations thereof.

Embodiment 24 is an embodiment of any of the preceding embodiments, wherein the tricyanohexane coproduct comprises a tetracyano compound having the chemical formula $C_xH_{2x-2}(CN)_4$;

wherein x is from 5 to 10.

Embodiment 25 is an embodiment of any of the preceding embodiments, wherein the composition comprises from 1 wppm to 10 wt. % tricyanohexane coproduct.

Embodiment 26 is an embodiment of any of the preceding embodiments, wherein the tricyanohexane coproduct comprises a tricyanoalkene.

Embodiment 27 is an embodiment of any of the preceding embodiments, wherein the tricyanohexane coproduct comprises a (cyanoethyl)amine.

Embodiment 28 is an embodiment of any of the preceding embodiments, wherein the cyanoethylamine comprises tri-(cyanoethyl)amine.

Embodiment 29 is an embodiment of any of the preceding embodiments, wherein the tricyanohexane coproduct comprises adiponitrile.

Embodiment 30 is an embodiment of any of the preceding embodiments, wherein the tricyanohexane coproduct comprises a cyanooxime having the chemical structure

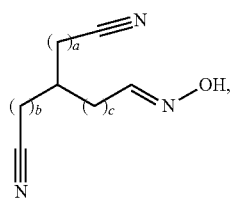

wherein a is 0 to 3, b is 1 to 3, and c is 1 to 4.

Embodiment 31 is an embodiment of any of the preceding embodiments, wherein the tricyanohexane coproduct comprises a cyano-compound having the chemical structure

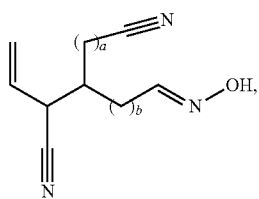

wherein a is from 1 to 3, and b is from 1 to 4.

Embodiment 32 is an embodiment of any of the preceding embodiments, wherein the tricyanohexane coproduct has a molecular weight ranging from 105 amu to 215 amu.

Embodiment 33 is an embodiment of any of the preceding embodiments, wherein the cyanocarbon composition comprises at least 92 wt. % tricyanohexane.

Embodiment 34 is an embodiment of any of the preceding embodiments, wherein the cyanocarbon composition comprises at least 92 wt. % tricyanohexane, from 0.1 wt % to 10 wt % of an isomer of tricyanohexane, wherein the weight ratio of tricyanohexane to the isomer is at least 5:1, and from 500 ppm to 1 wt % adiponitrile.

Embodiment 35 is an embodiment of any of the preceding embodiments, wherein the cyanocarbon composition comprises at least 92 wt. % tricyanohexane, from 0.5 wt % to 7 wt % of an isomer of tricyanohexane, and from 0.05 ppm to 2 wt. % of a tetracyano compound.

Embodiment 36 is a cyanocarbon composition comprising:
 at least 85 wt. % tricyanohexane;
 a first cyano-compound having the chemical formula $C_xH_{2x-2}(CN)_4$;
 a second cyano-compound having the chemical formula $C_6H_{11}(CN)_2(CNOH)$; and
 a third cyano-compound having the chemical formula $C_xH_{2x-3}(CN)_2(CNOH)$
 wherein x is independently from 5 to 10;
 wherein the weight ratio of the first cyano-compound to the second cyano-compound is less than 1;
 wherein the weight ratio of the second cyano-compound to the second cyano-compound is greater than 1.

Embodiment 37 is a cyanocarbon composition, comprising:
 tricyanohexane; and
 an in situ-formed coproduct comprising an isomer of tricyanohexane, a cyanoethylamine, an oxime of tricyanohexane, an amide of tricyanohexane, or a tetracyanoalkane, or combinations thereof.

Embodiment 38 is an embodiment of any of the preceding embodiments, wherein the composition comprises less than 0.1 wt. % tricyanohexane coproduct having a molecular weight ranging from 105 amu to 215 amu.

Embodiment 39 is an embodiment of any of the preceding embodiments, wherein the composition comprises at least 92 wt. % tricyanohexane, from 0.5 wt % to 7 wt % of an isomer of tricyanohexane, and from 0.05 ppm to 2 wt. % of a tetracyano compound, and wherein the isomer of tricyanohexane and the tetracyano compound are in situ-formed.

We claim:

1. A cyanocarbon composition comprising:
 1,3,6-tricyanohexane; and
 from 0.2 wt. % to 10 wt. % of a tricyanohexane coproduct selected from the group consisting of a tetracyano compound, a cyanoalkene, a cyanoamine, a cyanooxime, a cyanoamide, 1,2,3-tricyanohexane, 1,2,6-tricyanohexane, 1,3,4-tricyanohexane, 1,3,5-tricyanohexane, 1,4,5-tricyanohexane, 2,3,5-tricyanohexane, and combinations thereof.

2. The cyanocarbon composition of claim 1, wherein the tricyanohexane coproduct comprises an isomer of tricyanohexane selected from the group consisting of 1,2,3-tricyanohexane, 1,2,6-tricyanohexane, 1,3,4-tricyanohexane, 1,3,5-tricyanohexane, 1,4,5-tricyanohexane, 2,3,5-tricyanohexane, and combinations thereof.

3. The cyanocarbon composition of claim 2, wherein the weight ratio of tricyanohexane to the isomer is at least 5:1.

4. The cyanocarbon composition of claim 1, wherein the tricyanohexane coproduct comprises a tetracyano compound having the chemical formula $C_xH_{2x-2}(CN)_4$;
 wherein x is from 5 to 10.

5. The cyanocarbon composition of claim 4, wherein the composition comprises from 0.2 wt. % to 10 wt. % tricyanohexane coproduct.

6. The cyanocarbon composition of claim 1, wherein the tricyanohexane coproduct comprises a tricyanoalkene.

7. The cyanocarbon composition of claim 1, wherein the tricyanohexane coproduct comprises a (cyanoethyl)amine.

8. The cyanocarbon composition of claim 7, wherein the cyanoethylamine comprises tri-(cyanoethyl)amine.

9. The cyanocarbon composition of claim 1, wherein the tricyanohexane coproduct comprises adiponitrile.

10. The cyanocarbon composition of claim 1, wherein the tricyanohexane coproduct comprises a cyanooxime having the chemical structure

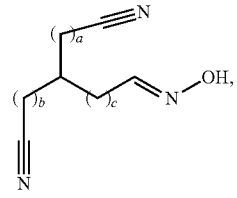

wherein a is 0 to 3, b is 1 to 3, and c is 1 to 4.

11. The cyanocarbon composition of claim 1, wherein the tricyanohexane coproduct comprises a cyano-compound having the chemical structure

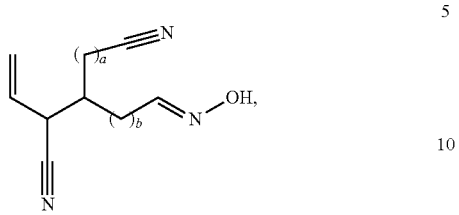

wherein a is from 1 to 3, and b is from 1 to 4.

12. The cyanocarbon composition of claim 1, wherein the tricyanohexane coproduct has a molecular weight ranging from 105 amu to 215 amu.

13. The cyanocarbon composition of claim 1, wherein the cyanocarbon composition comprises at least 92 wt. % 1,3,6-tricyanohexane.

14. The cyanocarbon composition of claim 2, wherein the cyanocarbon composition comprises at least 92 wt. % 1,3,6-tricyanohexane, from from 0.5 wt % to 7 wt % of the isomer of tricyanohexane, wherein the weight ratio of tricyanohexane to the isomer is at least 5:1, and from 500 ppm to 1 wt % adiponitrile.

15. The cyanocarbon composition of claim 2, wherein the cyanocarbon composition comprises at least 92 wt. % 1,3,6-tricyanohexane, from 0.5 wt % to 7 wt % of the isomer of tricyanohexane, and from 0.01 wt. % to 2 wt. % of a tetracyano compound.

\* \* \* \* \*